(12) United States Patent
Goedeke et al.

(10) Patent No.: US 10,576,273 B2
(45) Date of Patent: Mar. 3, 2020

(54) CATHETER AND CATHETER SYSTEM FOR ELECTRICAL NEUROMODULATION

(71) Applicant: Cardionomic, Inc., New Brighton, MN (US)

(72) Inventors: Steven D. Goedeke, Forest Lake, MN (US); Steven L. Waldhauser, Savage, MN (US); Charles L. Euteneuer, St. Michael, MN (US)

(73) Assignee: Cardionomic, Inc., New Brighton, MN (US)

( * ) Notice: Subject to any disclaimer, the term of this patent is extended or adjusted under 35 U.S.C. 154(b) by 7 days.

(21) Appl. No.: 15/357,510

(22) Filed: Nov. 21, 2016

(65) Prior Publication Data

US 2017/0065812 A1 Mar. 9, 2017

Related U.S. Application Data

(63) Continuation of application No. PCT/US2015/031960, filed on May 21, 2015.
(Continued)

(51) Int. Cl.
*A61N 1/05* (2006.01)
*A61M 25/10* (2013.01)
*A61N 1/36* (2006.01)

(52) U.S. Cl.
CPC ............. *A61N 1/057* (2013.01); *A61M 25/10* (2013.01); *A61N 1/36114* (2013.01)

(58) Field of Classification Search
CPC .............................. A61N 1/057; A61M 25/10
See application file for complete search history.

(56) References Cited

U.S. PATENT DOCUMENTS

| 4,718,423 A | 1/1988 | Willis et al. |
| 4,947,866 A | 8/1990 | Lessar et al. |

(Continued)

FOREIGN PATENT DOCUMENTS

| CA | 2 848 781 | 3/2013 |
| EP | 1 871 469 | 10/2013 |

(Continued)

OTHER PUBLICATIONS

U.S. Appl. No. 15/892,199, filed Feb. 8, 2018, Methods of Monitoring Effects of Neurostimulation.
(Continued)

*Primary Examiner* — Eric D. Bertram
(74) *Attorney, Agent, or Firm* — Knobbe Martens Olson & Bear, LLP

(57) ABSTRACT

A catheter having an elongate body, at least two elongate stimulation members extending from the elongate body, at least one electrode on each of the elongate stimulation members, where the electrodes form an electrode array that receives and conducts electrical current. The elongate stimulation members curve only in the first volume defined at least in part by a first plane, and a second volume defined at least in part by the first plane and being opposite the first volume can contain no electrodes. The catheter can further include a position gauge having a marking that indicates a length between a second end of the elongate body and a bumper end of the position gauge. The catheter can also include a pulmonary artery catheter having a lumen, where the catheter extends through the lumen of the pulmonary artery catheter.

20 Claims, 15 Drawing Sheets

Related U.S. Application Data

(60) Provisional application No. 62/001,729, filed on May 22, 2014.

(56) References Cited

U.S. PATENT DOCUMENTS

| | | | |
|---|---|---|---|
| 4,950,227 A | 8/1990 | Savin et al. |
| 5,067,957 A | 11/1991 | Jervis |
| 5,156,154 A | 10/1992 | Valenta, Jr. et al. |
| 5,190,546 A | 3/1993 | Jervis |
| 5,197,978 A | 3/1993 | Hess |
| 5,213,098 A | 5/1993 | Bennett et al. |
| 5,224,491 A | 7/1993 | Mehra |
| 5,259,387 A | 11/1993 | Depinto |
| 5,336,244 A | 8/1994 | Weijand |
| 5,345,936 A | 9/1994 | Pomeranz et al. |
| 5,365,926 A | 11/1994 | Desai |
| 5,383,852 A * | 1/1995 | Stevens-Wright ............ A61M 25/0136 604/95.04 |
| 5,423,881 A | 6/1995 | Breyen et al. |
| 5,431,649 A | 7/1995 | Mulier et al. |
| 5,462,527 A * | 10/1995 | Stevens-Wright ............ A61B 18/1492 600/585 |
| 5,554,139 A | 9/1996 | Okajima |
| 5,564,434 A | 10/1996 | Halperin et al. |
| 5,598,848 A | 2/1997 | Swanson et al. |
| 5,611,777 A * | 3/1997 | Bowden ............ A61M 25/0136 604/95.01 |
| 5,711,316 A | 1/1998 | Elsberry et al. |
| 5,725,570 A | 3/1998 | Heath |
| 5,755,766 A | 5/1998 | Chastain et al. |
| 5,782,239 A | 7/1998 | Webster |
| 5,853,411 A | 12/1998 | Whayne et al. |
| 5,948,007 A | 9/1999 | Starkebaum et al. |
| 5,954,761 A | 9/1999 | Machek et al. |
| 5,968,040 A * | 10/1999 | Swanson ................. A61N 1/00 600/374 |
| 5,997,563 A | 12/1999 | Kretzers |
| 6,036,697 A | 3/2000 | Dicaprio |
| 6,038,480 A | 3/2000 | Hrdlicka et al. |
| 6,058,331 A | 5/2000 | King et al. |
| 6,059,810 A | 5/2000 | Brown et al. |
| 6,071,308 A | 6/2000 | Ballou et al. |
| 6,136,021 A | 10/2000 | Tockman et al. |
| 6,152,882 A | 11/2000 | Prutchi |
| 6,161,029 A | 12/2000 | Spreigl et al. |
| 6,223,072 B1 | 4/2001 | Mika et al. |
| 6,231,516 B1 | 5/2001 | Keilman et al. |
| 6,233,484 B1 | 5/2001 | Ben-haim et al. |
| 6,233,487 B1 | 5/2001 | Mika et al. |
| 6,236,887 B1 | 5/2001 | Ben-haim et al. |
| 6,241,724 B1 | 6/2001 | Fleischman et al. |
| 6,254,610 B1 | 7/2001 | Darvish et al. |
| 6,263,242 B1 | 7/2001 | Mika et al. |
| 6,266,564 B1 | 7/2001 | Hill et al. |
| 6,285,906 B1 | 9/2001 | Ben-haim et al. |
| 6,292,693 B1 | 9/2001 | Darvish et al. |
| 6,292,695 B1 | 9/2001 | Webster et al. |
| 6,292,704 B1 | 9/2001 | Malonek et al. |
| 6,295,475 B1 | 9/2001 | Morgan |
| 6,298,268 B1 | 10/2001 | Ben-haim et al. |
| 6,304,777 B1 | 10/2001 | Ben-haim et al. |
| 6,317,631 B1 | 11/2001 | Ben-haim et al. |
| 6,319,241 B1 | 11/2001 | King et al. |
| 6,330,476 B1 | 12/2001 | Ben-haim et al. |
| 6,335,538 B1 | 1/2002 | Prutchi et al. |
| 6,348,045 B1 | 2/2002 | Malonek et al. |
| 6,353,762 B1 | 3/2002 | Baudino et al. |
| 6,360,123 B1 | 3/2002 | Kimchi et al. |
| 6,360,126 B1 | 3/2002 | Mika et al. |
| 6,363,279 B1 | 3/2002 | Ben-haim et al. |
| 6,370,430 B1 | 4/2002 | Mika et al. |
| 6,415,178 B1 | 7/2002 | Ben-haim et al. |
| 6,424,866 B2 | 7/2002 | Mika et al. |
| 6,428,537 B1 * | 8/2002 | Swanson ............ A61B 18/1492 606/41 |
| 6,442,424 B1 | 8/2002 | Ben-haim et al. |
| 6,447,478 B1 | 9/2002 | Maynard |
| 6,459,928 B2 | 10/2002 | Mika et al. |
| 6,463,324 B1 | 10/2002 | Ben-haim et al. |
| 6,473,653 B1 | 10/2002 | Schallhorn et al. |
| 6,480,737 B1 | 11/2002 | Policker et al. |
| 6,522,904 B1 | 2/2003 | Mika et al. |
| 6,522,926 B1 | 2/2003 | Kieval et al. |
| 6,529,778 B2 | 3/2003 | Prutchi |
| 6,542,774 B2 | 4/2003 | Hill et al. |
| 6,547,788 B1 | 4/2003 | Maguire et al. |
| 6,564,096 B2 | 5/2003 | Mest |
| 6,571,127 B1 | 5/2003 | Ben-haim et al. |
| 6,574,492 B1 | 6/2003 | Shlomo et al. |
| 6,587,721 B1 | 7/2003 | Prutchi et al. |
| 6,597,952 B1 | 7/2003 | Mika et al. |
| 6,600,953 B2 | 7/2003 | Flesler et al. |
| 6,662,055 B1 | 12/2003 | Prutchi |
| 6,669,693 B2 | 12/2003 | Friedman |
| 6,675,043 B1 | 1/2004 | Prutchi et al. |
| 6,684,105 B2 | 1/2004 | Cohen et al. |
| 6,694,192 B2 | 2/2004 | Policker et al. |
| 6,712,831 B1 | 3/2004 | Kaplan et al. |
| 6,725,093 B1 | 4/2004 | Ben-haim et al. |
| 6,738,655 B1 | 5/2004 | Sen et al. |
| 6,740,113 B2 | 5/2004 | Vrba |
| 6,748,271 B2 | 6/2004 | Spinelli et al. |
| 6,749,600 B1 | 6/2004 | Levy |
| 6,754,532 B1 | 6/2004 | Ferek-Petric |
| RE38,654 E | 11/2004 | Hill et al. |
| 6,832,478 B2 | 12/2004 | Anderson et al. |
| 6,850,801 B2 | 2/2005 | Kieval et al. |
| 6,887,266 B2 | 5/2005 | Williams et al. |
| 6,912,419 B2 | 6/2005 | Hill et al. |
| 6,932,930 B2 | 8/2005 | Desimone et al. |
| 6,944,490 B1 | 9/2005 | Chow |
| 6,947,792 B2 | 9/2005 | Ben-haim et al. |
| 6,950,689 B1 | 9/2005 | Willis et al. |
| 6,985,774 B2 | 1/2006 | Kieval et al. |
| 6,993,385 B1 | 1/2006 | Routh et al. |
| 7,027,863 B1 | 4/2006 | Prutchi et al. |
| 7,062,318 B2 | 6/2006 | Ben-haim et al. |
| 7,072,720 B2 | 7/2006 | Puskas |
| 7,082,336 B2 | 7/2006 | Ransbury et al. |
| 7,092,753 B2 | 8/2006 | Darvish et al. |
| 7,092,759 B2 | 8/2006 | Nehls et al. |
| 7,096,070 B1 | 8/2006 | Jenkins et al. |
| 7,097,665 B2 | 8/2006 | Stack et al. |
| 7,111,627 B2 | 9/2006 | Stack et al. |
| 7,121,283 B2 | 10/2006 | Stack et al. |
| 7,141,061 B2 | 11/2006 | Williams et al. |
| 7,146,984 B2 | 12/2006 | Stack et al. |
| 7,152,607 B2 | 12/2006 | Stack et al. |
| 7,158,832 B2 | 1/2007 | Kieval et al. |
| 7,163,554 B2 | 1/2007 | Williams et al. |
| 7,167,748 B2 | 1/2007 | Ben-haim et al. |
| 7,171,263 B2 | 1/2007 | Darvish et al. |
| 7,187,970 B2 | 3/2007 | Shemer et al. |
| 7,190,997 B1 | 3/2007 | Darvish et al. |
| 7,195,594 B2 | 3/2007 | Eigler et al. |
| 7,195,637 B2 | 3/2007 | Mika |
| 7,218,963 B2 | 5/2007 | Ben-haim et al. |
| 7,231,260 B2 | 6/2007 | Wallace et al. |
| 7,260,431 B2 | 8/2007 | Libbus et al. |
| 7,277,757 B2 | 10/2007 | Casavant et al. |
| 7,277,761 B2 | 10/2007 | Shelchuk |
| 7,279,007 B2 | 10/2007 | Nikolic |
| 7,285,287 B2 | 10/2007 | Williams et al. |
| 7,295,881 B2 | 11/2007 | Cohen et al. |
| 7,308,303 B2 | 12/2007 | Whitehurst et al. |
| 7,310,555 B2 | 12/2007 | Ben-haim et al. |
| 7,321,793 B2 | 1/2008 | Ben Ezra et al. |
| 7,354,454 B2 | 4/2008 | Stack et al. |
| 7,363,082 B2 | 4/2008 | Ransbury et al. |
| 7,377,939 B2 | 5/2008 | Williams et al. |
| 7,389,149 B2 | 6/2008 | Rossing et al. |

(56) References Cited

U.S. PATENT DOCUMENTS

| | | |
|---|---|---|
| 7,412,289 B2 | 8/2008 | Malonek et al. |
| 7,431,725 B2 | 10/2008 | Stack et al. |
| 7,460,906 B2 | 12/2008 | Libbus |
| 7,460,907 B1 | 12/2008 | Darvish et al. |
| 7,486,991 B2 | 2/2009 | Libbus et al. |
| 7,499,742 B2 | 3/2009 | Bolea et al. |
| 7,509,166 B2 | 3/2009 | Libbus |
| 7,529,589 B2 | 5/2009 | Williams et al. |
| 7,542,800 B2 | 6/2009 | Libbus et al. |
| 7,547,286 B2 | 6/2009 | Choate |
| 7,561,923 B2 | 7/2009 | Libbus et al. |
| 7,616,997 B2 | 11/2009 | Kieval et al. |
| 7,617,003 B2 | 11/2009 | Caparso et al. |
| 7,617,007 B2 | 11/2009 | Williams et al. |
| 7,623,926 B2 | 11/2009 | Rossing et al. |
| 7,630,760 B2 | 12/2009 | Libbus et al. |
| 7,634,317 B2 | 12/2009 | Ben-David et al. |
| 7,643,875 B2 | 1/2010 | Heil, Jr. et al. |
| 7,647,102 B2 | 1/2010 | Routh et al. |
| 7,658,709 B2 | 2/2010 | Anderson et al. |
| 7,668,602 B2 | 2/2010 | Ben-David et al. |
| 7,676,266 B1 | 3/2010 | Kroll |
| 7,704,276 B2 | 4/2010 | Williams et al. |
| 7,706,884 B2 | 4/2010 | Libbus |
| 7,734,343 B2 | 6/2010 | Ransbury et al. |
| 7,734,348 B2 | 6/2010 | Zhang et al. |
| 7,747,335 B2 * | 6/2010 | Williams ......... A61M 5/14276 607/115 |
| 7,765,000 B2 | 7/2010 | Zhang et al. |
| 7,769,446 B2 | 8/2010 | Moffitt et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,801,614 B2 | 9/2010 | Rossing et al. |
| 7,805,194 B1 | 9/2010 | Schecter |
| 7,805,203 B2 | 9/2010 | Ben-David et al. |
| 7,813,812 B2 | 10/2010 | Kieval et al. |
| 7,840,262 B2 | 11/2010 | Mika et al. |
| 7,840,271 B2 | 11/2010 | Kieval et al. |
| 7,840,282 B2 | 11/2010 | Williams et al. |
| 7,848,812 B2 | 12/2010 | Crowley et al. |
| 7,857,748 B2 | 12/2010 | Williams et al. |
| 7,869,881 B2 | 1/2011 | Libbus et al. |
| 7,873,413 B2 | 1/2011 | McCabe et al. |
| 7,881,782 B2 | 2/2011 | Libbus et al. |
| 7,885,709 B2 | 2/2011 | Ben-David |
| 7,885,711 B2 | 2/2011 | Ben-Ezra et al. |
| 7,890,185 B2 | 2/2011 | Cohen et al. |
| 7,892,292 B2 | 2/2011 | Stack et al. |
| 7,899,554 B2 | 3/2011 | Williams et al. |
| 7,904,151 B2 | 3/2011 | Ben-David et al. |
| 7,904,176 B2 | 3/2011 | Ben-Ezra et al. |
| 7,908,008 B2 | 3/2011 | Ben-David et al. |
| 7,919,162 B2 | 4/2011 | Desimone et al. |
| 7,925,352 B2 | 4/2011 | Stack et al. |
| 7,949,400 B2 | 5/2011 | Kieval et al. |
| 7,953,481 B1 | 5/2011 | Shemer et al. |
| 7,966,067 B2 | 6/2011 | Rousso et al. |
| 7,974,693 B2 | 7/2011 | Ben-David et al. |
| 8,000,793 B2 | 8/2011 | Libbus |
| 8,005,542 B2 | 8/2011 | Ben-Ezra et al. |
| 8,005,545 B2 | 8/2011 | Ben-David et al. |
| 8,014,858 B1 | 9/2011 | Ben-haim et al. |
| 8,014,874 B2 | 9/2011 | Rossing et al. |
| 8,024,050 B2 | 9/2011 | Libbus et al. |
| 8,027,724 B2 | 9/2011 | Wei et al. |
| 8,032,215 B2 | 10/2011 | Libbus et al. |
| 8,036,745 B2 | 10/2011 | Ben-David et al. |
| 8,060,197 B2 | 11/2011 | Ben-David et al. |
| 8,060,206 B2 | 11/2011 | Kieval et al. |
| 8,060,218 B2 | 11/2011 | Singh et al. |
| 8,086,314 B1 | 12/2011 | Kieval |
| 8,116,881 B2 | 2/2012 | Cohen et al. |
| 8,116,883 B2 | 2/2012 | Williams et al. |
| 8,118,751 B2 | 2/2012 | Dobak, III |
| 8,121,693 B2 | 2/2012 | Libbus |
| 8,126,560 B2 | 2/2012 | Schiener et al. |
| 8,131,373 B2 | 3/2012 | Libbus |
| 8,145,304 B2 | 3/2012 | Moffitt et al. |
| 8,150,521 B2 | 4/2012 | Crowley et al. |
| 8,152,843 B2 | 4/2012 | Williams et al. |
| 8,155,744 B2 | 4/2012 | Rezai |
| 8,175,705 B2 | 5/2012 | Libbus |
| 8,195,289 B2 | 6/2012 | Heil, Jr. et al. |
| 8,195,290 B2 | 6/2012 | Brockway et al. |
| 8,204,591 B2 | 6/2012 | Ben-David et al. |
| 8,204,596 B2 | 6/2012 | Ransbury et al. |
| 8,206,456 B2 | 6/2012 | Stack et al. |
| 8,224,444 B2 | 7/2012 | Ben-David et al. |
| 8,229,564 B2 | 7/2012 | Rezai |
| 8,239,037 B2 | 8/2012 | Glenn et al. |
| 8,239,045 B2 | 8/2012 | Ransbury et al. |
| 8,244,355 B2 | 8/2012 | Bennett et al. |
| 8,249,706 B2 | 8/2012 | Koh |
| 8,260,416 B2 | 9/2012 | Ben-haim et al. |
| 8,290,595 B2 | 10/2012 | Kieval et al. |
| 8,301,247 B2 | 10/2012 | Ben-haim et al. |
| 8,306,616 B2 | 11/2012 | Ben-haim et al. |
| 8,306,617 B2 | 11/2012 | Ben-haim et al. |
| 8,311,629 B2 | 11/2012 | Ben-haim et al. |
| 8,311,633 B2 | 11/2012 | Ransbury et al. |
| 8,321,013 B2 | 11/2012 | Darvish et al. |
| 8,326,416 B2 | 12/2012 | Mika et al. |
| 8,335,571 B2 | 12/2012 | Singh et al. |
| 8,352,031 B2 | 1/2013 | Rousso et al. |
| 8,369,954 B2 | 2/2013 | Stack et al. |
| 8,372,325 B2 | 2/2013 | Williams et al. |
| 8,386,053 B2 | 2/2013 | Kornet |
| 8,386,056 B2 | 2/2013 | Ben-David et al. |
| 8,401,672 B2 | 3/2013 | Libbus et al. |
| 8,406,864 B2 | 3/2013 | Rousso et al. |
| 8,406,877 B2 | 3/2013 | Smith et al. |
| 8,412,326 B2 | 4/2013 | Arcot-Krishnamurthy et al. |
| 8,417,354 B2 | 4/2013 | Zhang et al. |
| 8,428,730 B2 | 4/2013 | Stack et al. |
| 8,437,867 B2 | 5/2013 | Murney et al. |
| 8,452,398 B2 | 5/2013 | Libbus et al. |
| 8,473,076 B2 | 6/2013 | Libbus et al. |
| 8,498,703 B2 | 7/2013 | Spinelli et al. |
| 8,538,535 B2 | 9/2013 | Gross et al. |
| 8,548,583 B2 | 10/2013 | Rousso et al. |
| 8,565,896 B2 | 10/2013 | Ben-David et al. |
| 8,571,651 B2 | 10/2013 | Ben-Ezra et al. |
| 8,571,653 B2 | 10/2013 | Ben-David et al. |
| 8,583,236 B2 | 11/2013 | Kieval et al. |
| 8,606,359 B2 | 12/2013 | Rossing et al. |
| 8,609,082 B2 | 12/2013 | Ben-David et al. |
| 8,615,294 B2 | 12/2013 | Ben-David et al. |
| 8,620,426 B2 | 12/2013 | Moffitt et al. |
| 8,626,290 B2 | 1/2014 | Dagan et al. |
| 8,626,299 B2 | 1/2014 | Gross et al. |
| 8,634,921 B2 | 1/2014 | Chavan et al. |
| 8,639,332 B2 | 1/2014 | Kuhn et al. |
| 8,655,444 B2 | 2/2014 | Ben-haim et al. |
| 8,682,430 B2 | 3/2014 | Libbus et al. |
| 8,682,434 B2 | 3/2014 | Libbus |
| 8,706,230 B2 | 4/2014 | Rousso et al. |
| 8,712,531 B2 | 4/2014 | Kieval et al. |
| 8,718,789 B2 | 5/2014 | Bolea et al. |
| 8,725,250 B2 | 5/2014 | Brockway et al. |
| 8,755,907 B2 | 6/2014 | Kieval et al. |
| 8,771,337 B2 | 7/2014 | Williams et al. |
| 8,784,354 B2 | 7/2014 | Stack et al. |
| 8,784,500 B2 | 7/2014 | Stack et al. |
| 8,788,066 B2 | 7/2014 | Cates et al. |
| 8,798,738 B2 | 8/2014 | Machado et al. |
| 8,805,501 B2 | 8/2014 | Libbus |
| 8,818,501 B2 * | 8/2014 | Machado ........... A61N 1/36114 607/2 |
| 8,825,152 B2 | 9/2014 | Shemer et al. |
| 8,838,246 B2 | 9/2014 | Kieval |
| 8,855,783 B2 | 10/2014 | Dagan et al. |
| 8,880,190 B2 | 11/2014 | Kieval et al. |
| 8,886,340 B2 | 11/2014 | Williams et al. |

(56) References Cited

U.S. PATENT DOCUMENTS

| | | |
|---|---|---|
| 8,901,878 B2 | 12/2014 | Prutchi et al. |
| 8,906,286 B2 | 12/2014 | Desimone et al. |
| 8,918,172 B2 | 12/2014 | Moffitt et al. |
| 8,929,990 B2 | 1/2015 | Moffitt et al. |
| 8,934,956 B2 | 1/2015 | Glenn et al. |
| 8,934,968 B2 | 1/2015 | Whitehurst et al. |
| 8,958,872 B2 | 2/2015 | Ben-haim et al. |
| 8,972,015 B2 | 3/2015 | Stack et al. |
| 8,977,353 B2 | 3/2015 | Rousso et al. |
| 8,983,601 B2 | 3/2015 | Fukamachi et al. |
| 9,005,100 B2 | 4/2015 | Gnanashanmugam et al. |
| 9,005,106 B2 | 4/2015 | Gross et al. |
| 9,011,751 B2 | 4/2015 | Williams et al. |
| 9,031,650 B2 | 5/2015 | McCabe et al. |
| 9,031,669 B2 | 5/2015 | Zhang et al. |
| 9,044,609 B2 | 6/2015 | Bolea et al. |
| 9,067,071 B2 | 6/2015 | Sanders et al. |
| 9,126,048 B2 | 9/2015 | Ransbury et al. |
| 9,149,639 B2 | 10/2015 | Zhang et al. |
| 9,168,094 B2 | 10/2015 | Lee et al. |
| 9,180,035 B2 | 11/2015 | Stack et al. |
| 9,186,514 B2 | 11/2015 | Ben-haim et al. |
| 9,216,289 B2 | 12/2015 | Libbus et al. |
| 9,248,038 B2 | 2/2016 | Stack et al. |
| 9,289,618 B1 | 3/2016 | Ben-haim et al. |
| 9,446,240 B2 | 9/2016 | Masson et al. |
| 9,480,790 B2 | 11/2016 | Machado et al. |
| 9,494,960 B2 | 11/2016 | Weerakoon et al. |
| 9,504,833 B2 | 11/2016 | Kramer et al. |
| 9,511,229 B2 | 12/2016 | Bradley |
| 9,517,350 B2 | 12/2016 | Ternes et al. |
| 9,545,512 B2 | 1/2017 | Williams et al. |
| 9,597,515 B2 | 3/2017 | Rockweiler et al. |
| 9,610,012 B2 | 4/2017 | Bardy |
| 9,622,665 B2 | 4/2017 | Zhang et al. |
| 9,623,252 B2 | 4/2017 | Sathaye et al. |
| 9,636,503 B2 | 5/2017 | Mokelke et al. |
| 9,656,089 B2 | 5/2017 | Yip et al. |
| 9,687,653 B2 | 6/2017 | Woods et al. |
| 9,707,076 B2 | 7/2017 | Stack et al. |
| 9,717,899 B2 | 8/2017 | Kuzma et al. |
| 9,731,135 B2 | 8/2017 | Arcot-Krishnamurthy et al. |
| 9,737,228 B2 | 8/2017 | Mahajan et al. |
| 9,782,591 B2 | 10/2017 | Kramer et al. |
| 9,814,883 B2 | 11/2017 | Marnfeldt et al. |
| 9,833,608 B2 | 12/2017 | Masson |
| 9,844,453 B2 | 12/2017 | Stack et al. |
| 9,848,795 B2 | 12/2017 | Marecki et al. |
| 9,849,290 B2 | 12/2017 | Zhao et al. |
| 9,855,317 B2 | 1/2018 | Bright |
| 9,861,435 B2 | 1/2018 | Richardson et al. |
| 9,878,150 B2 | 1/2018 | Machado et al. |
| 9,884,182 B2 | 2/2018 | Ransbury et al. |
| 10,172,549 B2 | 1/2019 | Waldhauser et al. |
| 10,188,343 B2 | 1/2019 | Goedeke et al. |
| 10,322,000 B2 | 6/2019 | Orth et al. |
| 2002/0087192 A1 | 7/2002 | Barrett et al. |
| 2003/0045909 A1 | 3/2003 | Gross et al. |
| 2003/0114739 A1 | 6/2003 | Fuimaono et al. |
| 2003/0114878 A1 | 6/2003 | Diederich et al. |
| 2003/0216792 A1 | 11/2003 | Levin et al. |
| 2003/0233099 A1 | 12/2003 | Danaek et al. |
| 2004/0098090 A1 | 5/2004 | Williams et al. |
| 2004/0143254 A1 | 7/2004 | Vanney et al. |
| 2004/0172079 A1 | 9/2004 | Chinchoy |
| 2004/0172094 A1 | 9/2004 | Cohen et al. |
| 2004/0181136 A1 | 9/2004 | McDaniel et al. |
| 2004/0193231 A1 | 9/2004 | David et al. |
| 2004/0215233 A1 | 10/2004 | Kaplan et al. |
| 2004/0260375 A1 | 12/2004 | Zhang et al. |
| 2005/0065553 A1 | 3/2005 | Ben Ezra et al. |
| 2005/0119752 A1 | 6/2005 | Williams et al. |
| 2005/0142315 A1 | 6/2005 | Desimone et al. |
| 2005/0154321 A1 | 7/2005 | Wolinsky et al. |
| 2005/0187556 A1 | 8/2005 | Stack et al. |
| 2005/0187586 A1 | 8/2005 | David et al. |
| 2005/0187615 A1 | 8/2005 | Williams et al. |
| 2005/0197675 A1 | 9/2005 | David et al. |
| 2005/0247320 A1 | 11/2005 | Stack et al. |
| 2005/0251239 A1 | 11/2005 | Wallace et al. |
| 2005/0267542 A1 | 12/2005 | David et al. |
| 2005/0271794 A1 | 12/2005 | Desimone et al. |
| 2005/0273146 A1 | 12/2005 | Desimone et al. |
| 2006/0058597 A1 | 3/2006 | Machado et al. |
| 2006/0074453 A1 | 4/2006 | Kieval et al. |
| 2006/0085046 A1 | 4/2006 | Rezai et al. |
| 2006/0100668 A1 | 5/2006 | Ben-David et al. |
| 2006/0116737 A1 | 6/2006 | Libbus |
| 2006/0206159 A1 | 9/2006 | Moffitt et al. |
| 2006/0229677 A1 | 10/2006 | Moffitt et al. |
| 2006/0259084 A1 | 11/2006 | Zhang et al. |
| 2006/0259085 A1 | 11/2006 | Zhang et al. |
| 2007/0023951 A1 | 2/2007 | Williams et al. |
| 2007/0027527 A1 | 2/2007 | Williams et al. |
| 2007/0060932 A1 | 3/2007 | Stack et al. |
| 2007/0135875 A1 | 6/2007 | Demarais et al. |
| 2007/0255364 A1 | 11/2007 | Gerber et al. |
| 2008/0015659 A1 | 1/2008 | Zhang et al. |
| 2008/0046016 A1 | 2/2008 | Ben-David et al. |
| 2008/0082137 A1 | 4/2008 | Kieval et al. |
| 2008/0086182 A1 | 4/2008 | Ben-David et al. |
| 2008/0091240 A1 | 4/2008 | Ben-David et al. |
| 2008/0091241 A1 | 4/2008 | Ben-Ezra et al. |
| 2008/0091245 A1 | 4/2008 | Ben-Ezra et al. |
| 2008/0119898 A1 | 5/2008 | Ben-David et al. |
| 2008/0125819 A1 | 5/2008 | Ben-David et al. |
| 2008/0125825 A1 | 5/2008 | Ben-Ezra et al. |
| 2008/0125827 A1 | 5/2008 | Ben-David et al. |
| 2008/0125843 A1 | 5/2008 | Ben-David et al. |
| 2008/0132964 A1 | 6/2008 | Cohen et al. |
| 2008/0132983 A1 | 6/2008 | Cohen et al. |
| 2008/0140141 A1 | 6/2008 | Ben-David et al. |
| 2008/0161894 A1 | 7/2008 | Ben-David et al. |
| 2008/0167693 A1 | 7/2008 | Kieval et al. |
| 2008/0177338 A1 | 7/2008 | Ben-David et al. |
| 2008/0215008 A1 | 9/2008 | Nance et al. |
| 2008/0275349 A1 | 11/2008 | Halperin et al. |
| 2008/0275514 A1 | 11/2008 | Ben-David et al. |
| 2008/0312711 A1 | 12/2008 | Struble |
| 2009/0012542 A1 | 1/2009 | N'diaye et al. |
| 2009/0012546 A1 | 1/2009 | N'diaye et al. |
| 2009/0018596 A1 | 1/2009 | Kieval |
| 2009/0022078 A1 | 1/2009 | Zhang et al. |
| 2009/0096137 A1 | 4/2009 | Williams et al. |
| 2009/0105823 A1 | 4/2009 | Williams et al. |
| 2009/0163912 A1 | 6/2009 | Wang et al. |
| 2009/0228078 A1 | 9/2009 | Zhang et al. |
| 2009/0276022 A1* | 11/2009 | Burnes ............... A61N 1/0558 607/116 |
| 2009/0281608 A1 | 11/2009 | Foster |
| 2010/0069768 A1 | 3/2010 | Min et al. |
| 2010/0222832 A1 | 9/2010 | Zhang et al. |
| 2011/0004198 A1 | 1/2011 | Hoch |
| 2011/0106199 A1 | 5/2011 | McCabe et al. |
| 2011/0118726 A1 | 5/2011 | de la Rama et al. |
| 2011/0153030 A1 | 6/2011 | Stack et al. |
| 2011/0160790 A1 | 6/2011 | Stegemann et al. |
| 2012/0029510 A1 | 2/2012 | Haverkost |
| 2012/0197141 A1 | 8/2012 | Vanney et al. |
| 2012/0232563 A1 | 9/2012 | Williams et al. |
| 2012/0253280 A1* | 10/2012 | Pantin ............... A61M 25/007 604/96.01 |
| 2012/0303080 A1 | 11/2012 | Ben-David et al. |
| 2012/0310304 A1 | 12/2012 | Brockway et al. |
| 2013/0012863 A1 | 1/2013 | Stack et al. |
| 2013/0110208 A1 | 5/2013 | Inagaki et al. |
| 2013/0172715 A1 | 7/2013 | Just et al. |
| 2013/0218221 A1 | 8/2013 | Zhang et al. |
| 2013/0226272 A1 | 8/2013 | Cattaneo et al. |
| 2013/0253616 A1 | 9/2013 | Libbus et al. |
| 2013/0289358 A1 | 10/2013 | Melsky et al. |
| 2013/0289686 A1 | 10/2013 | Masson et al. |
| 2013/0331919 A1 | 12/2013 | Zhang et al. |
| 2013/0338748 A1 | 12/2013 | Dagan |

(56) References Cited

U.S. PATENT DOCUMENTS

| | | |
|---|---|---|
| 2014/0012242 A1 | 1/2014 | Lee et al. |
| 2014/0046407 A1 | 2/2014 | Ben-Ezra et al. |
| 2014/0052208 A1 | 2/2014 | Ransbury et al. |
| 2014/0074148 A1 | 3/2014 | Glenn et al. |
| 2014/0114377 A1 | 4/2014 | Dagan et al. |
| 2014/0128750 A1 | 5/2014 | Ransbury et al. |
| 2014/0172006 A1 | 6/2014 | Stack et al. |
| 2014/0214135 A1 | 7/2014 | Ben-David et al. |
| 2014/0222031 A1 | 8/2014 | Stack et al. |
| 2014/0222125 A1 | 8/2014 | Glenn et al. |
| 2014/0277235 A1 | 9/2014 | An et al. |
| 2014/0324115 A1 | 10/2014 | Ziegler et al. |
| 2015/0018908 A1 | 1/2015 | Williams et al. |
| 2015/0039058 A1 | 2/2015 | Masson et al. |
| 2015/0066133 A1 | 3/2015 | Desimone et al. |
| 2015/0105645 A1 | 4/2015 | Subramaniam et al. |
| 2015/0134019 A1 | 5/2015 | Moffitt et al. |
| 2015/0142011 A1 | 5/2015 | Cates et al. |
| 2015/0150508 A1 | 6/2015 | Glenn et al. |
| 2015/0151121 A1 | 6/2015 | Dagan et al. |
| 2015/0157777 A1 | 6/2015 | Tuval et al. |
| 2015/0164662 A1 | 6/2015 | Tuval |
| 2015/0238763 A1 | 8/2015 | Bolea et al. |
| 2015/0306395 A1 | 10/2015 | Libbus et al. |
| 2016/0022890 A1 | 1/2016 | Schwammenthal et al. |
| 2016/0051741 A1 | 2/2016 | Schwammenthal et al. |
| 2016/0174864 A1 | 6/2016 | Levin et al. |
| 2017/0001015 A1 | 1/2017 | Marnfeldt et al. |
| 2017/0027458 A1 | 2/2017 | Glover et al. |
| 2017/0036014 A1 | 2/2017 | Machado et al. |
| 2017/0065818 A1 | 3/2017 | Ransbury et al. |
| 2017/0143227 A1 | 5/2017 | Marecki et al. |
| 2017/0173338 A1 | 6/2017 | Waldhauser et al. |
| 2017/0173339 A1 | 6/2017 | Waldhauser et al. |
| 2017/0189642 A1 | 7/2017 | Masson et al. |
| 2017/0224999 A1 | 8/2017 | Yip et al. |
| 2017/0258337 A1 | 9/2017 | Libbus et al. |
| 2017/0291023 A1 | 10/2017 | Kuzma et al. |
| 2017/0296086 A1 | 10/2017 | Ternes et al. |
| 2017/0312525 A1 | 11/2017 | Masson et al. |
| 2017/0325881 A1 | 11/2017 | Richardson et al. |
| 2018/0050190 A1 | 2/2018 | Masson |
| 2018/0050206 A1 | 2/2018 | Waldhauser et al. |
| 2018/0147408 A1 | 5/2018 | Machado et al. |
| 2018/0161577 A1 | 6/2018 | Goedeke et al. |
| 2018/0168503 A1 | 6/2018 | Waldhauser et al. |
| 2018/0169414 A1 | 6/2018 | Goedeke et al. |
| 2018/0214696 A1 | 8/2018 | Cuchiara et al. |
| 2018/0214697 A1 | 8/2018 | Cuchiara et al. |
| 2018/0214698 A1 | 8/2018 | Cuchiara et al. |
| 2018/0236220 A1 | 8/2018 | Glenn et al. |
| 2019/0150832 A1 | 5/2019 | Goedeke |
| 2019/0186702 A1 | 6/2019 | Masson |

FOREIGN PATENT DOCUMENTS

| | | |
|---|---|---|
| EP | 2 316 525 | 1/2016 |
| EP | 2 731 671 | 4/2019 |
| JP | 2001-505450 | 4/2001 |
| JP | 2004-160219 | 6/2004 |
| JP | 2008-526456 | 7/2008 |
| JP | 2009-508594 | 3/2009 |
| JP | 2011-147791 | 8/2011 |
| WO | WO 1997/024983 | 7/1997 |
| WO | WO 2005/041748 | 5/2005 |
| WO | WO 2006/007048 | 1/2006 |
| WO | WO 2006/058253 | 6/2006 |
| WO | WO 2007/052341 | 5/2007 |
| WO | WO 2008/054448 | 5/2008 |
| WO | WO 2009/135083 | 11/2009 |
| WO | WO 2012/068273 | 5/2012 |
| WO | WO 2012/149511 | 11/2012 |
| WO | WO 2015/179634 | 11/2015 |
| WO | WO 2016/040037 | 3/2016 |
| WO | WO 2016/040038 | 3/2016 |
| WO | WO 2016/111940 | 7/2016 |
| WO | WO 2016/195477 | 12/2016 |
| WO | WO 2017/156039 | 9/2017 |

OTHER PUBLICATIONS

U.S. Appl. No. 15/893,038, filed Feb. 9, 2018, Methods of Facilitating Positioning of Electrodes.

Lawo et al., "Electrical Signals Applied During the Absolute Refractory Period", JACC, Dec. 20, 2005, vol. 46, No. 21, pp. 2229-2236.

Rudski et al., "Guidelines for the Echocardiographic Assessment of the Right Heart in Adults: A Report from the American Society of Echocardiography", J Am Soc Echocardiogr, 2010, vol. 23, pp. 685-713.

International Search Report and Written Opinion issued in PCT Application No. PCT/US2015/031960, dated Mar. 1, 2016, in 14 pages.

Fornell, "Multi-Electrode RF Balloon Efficient for Acute Pulmonary Vein Isolation", Ablation Systems, May 17, 2017, http://www.dicardiology.com/article/multi-electrode-rf-balloon-efficient-acute-pulmonary-vein-isolation?sthash.wVTUprIW.mjjo, downloaded on Oct. 30, 2017.

Ardell et al., "Differential sympathetic regulation of automatic, conductile, and contractile tissue in dog heart," American Journal of Physiology (Nov. 1988) 255 (5): H1050-H1059.

Casadei, "Vagal control of myocardial . . . in humans," The Physiological Society (Mar. 2001): 817-823.

De Ferrari et al., "Vagus nerve stimulation . . . future directions," Heart Fail Rev. (2011) 16: 195-203.

Klein et al., "Vagus nerve stimulation . . . heart failure," Cariology Journal (2010) 17 (6): 638-643.

Koizumi et al., "Functional significance of coactivation . . . ," National Academy of Sciences (Mar. 1982) 79 (6): 2116-2120.

Meyer et al., "Augmentation of left ventricular . . . ," Americ. Heart Assoc. (2010): 1286-1294.

Murphy, "Preliminary observations of the effects of simulation of . . . in man," CA Journal of Phys. and Pharmac (Jun. 1985). 63 (6): 649-655.

Randall et al., "Regional cardiac distribution . . . ," Federation Proceedings (Jul.-Aug. 1972) 31 (4): 1199-1208.

Randall, "Augmentor action to the sympathetic . . . ," Journal of Applied Physiology (Jul. 1960) 15 (4): 629-631.

Triposkiadis et al., "Sympathetic nervous . . . failure," Journal of Amer. Coll. of Cardiology (Nov. 3, 2009) 54 (19): 1747-1762.

Zarse, "Selective increase . . . sympathetic tone," Journal of Amer. Coll. of Cardiology (2005) 46 (7): 1354-1359.

U.S. Appl. No. 15/334,121, filed Oct. 25, 2016, Methods and Systems for Increasing Heart Contractility by Neuromodulation.

U.S. Appl. No. 15/334,121, filed Oct. 25, 2016, Methods and Systems for Treating Acute Heart Failure by Neuromodulation.

Karamanoglu, "A System for Analysis of Arterial Blood Pressure Waveforms in Humans", Computers and Biomedical Research, 1997, vol. 30, pp. 244-255.

Karamanoglu et al., "Estimation of cardiac output in patients with congestive heart failure by analysis of right ventricular pressure waveforms", Biomedical Engineering Online, 2011, vol. 10, No. 36.

Karamanoglu et al., "Right Ventricular Pressure Waveform and Wave Reflection Analysis in Patients With Pulmonary Arterial Hypertension", Chest Jour., Jul. 2007, vol. 132, No. 1, pp. 37-43.

U.S. Appl. No. 11/951,285, filed Dec. 5, 2007, Methods and Systems for Treating Acute Heart Failure by Neuromodulation.

U.S. Appl. No. 12/185,473 (U.S. Pat. No. 8,818,501), filed Aug. 4, 2008 (dated Aug. 26, 2014), Methods and Systems for Treating Acute Heart Failure by Neuromodulation.

U.S. Appl. No. 13/654,525 (U.S. Pat. No. 8,798,738), filed Oct. 18, 2012 (dated Aug. 5, 2014), Methods and Systems for Treating Acute Heart Failure by Neuromodulation.

U.S. Appl. No. 14/085,311 (U.S. Pat. No. 9,480,790), filed Nov. 20, 2013 (dated Nov. 1, 2016), Methods and Systems for Treating Acute Heart Failure by Neuromodulation.

(56) References Cited

OTHER PUBLICATIONS

U.S. Appl. No. 15/334,121 (U.S. Pat. No. 9,878,150), filed Oct. 25, 2016 (dated Jan. 30, 2018), Methods and Systems for Increasing Heart Contractility by Neuromodulation.
U.S. Appl. No. 15/879,694, filed Jan. 25, 2018, Methods and Systems for Increasing Heart Contractility by Neuromodulation.
U.S. Appl. No. 15/446,872, filed Mar. 1, 2017, Catheter and Electrode Systems for Electrical Neuromodulation.
U.S. Appl. No. 15/446,881, filed Mar. 1, 2017, Methods for Electrical Neuromodulation of the Heart.
U.S. Appl. No. 15/540,161, filed Jun. 27, 2017, Cardiac Modulation Facilitation Methods and Systems.
U.S. Appl. No. 15/892,135, filed Feb. 8, 2018, Methods of Reducing Duty Cycle During Neurostimulation Treatment.
U.S. Appl. No. 15/892,199 (U.S. Pat. No. 10,188,343), filed Feb. 8, 2018 (dated Jan. 9, 2019), Methods of Monitoring Effects of Neurostimulation.
U.S. Appl. No. 15/893,038 (U.S. Pat. No. 10,172,549), filed Feb. 9, 2018 (dated Jan. 8, 2019), Methods of Facilitating Positioning of Electrodes.
U.S. Appl. No. 16/259,306, filed Jan. 28, 2019, Neurostimulation Devices and Methods.

* cited by examiner

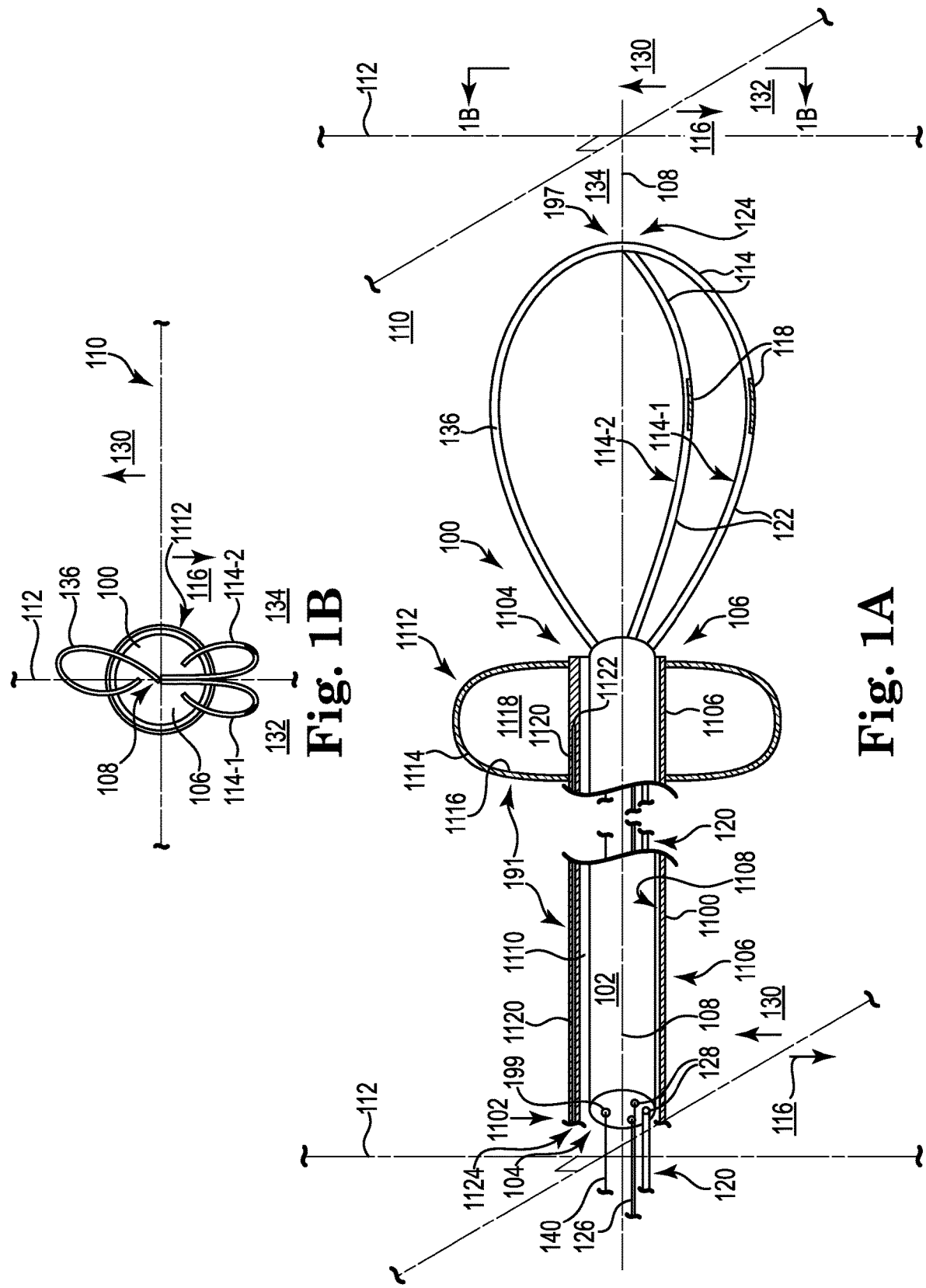

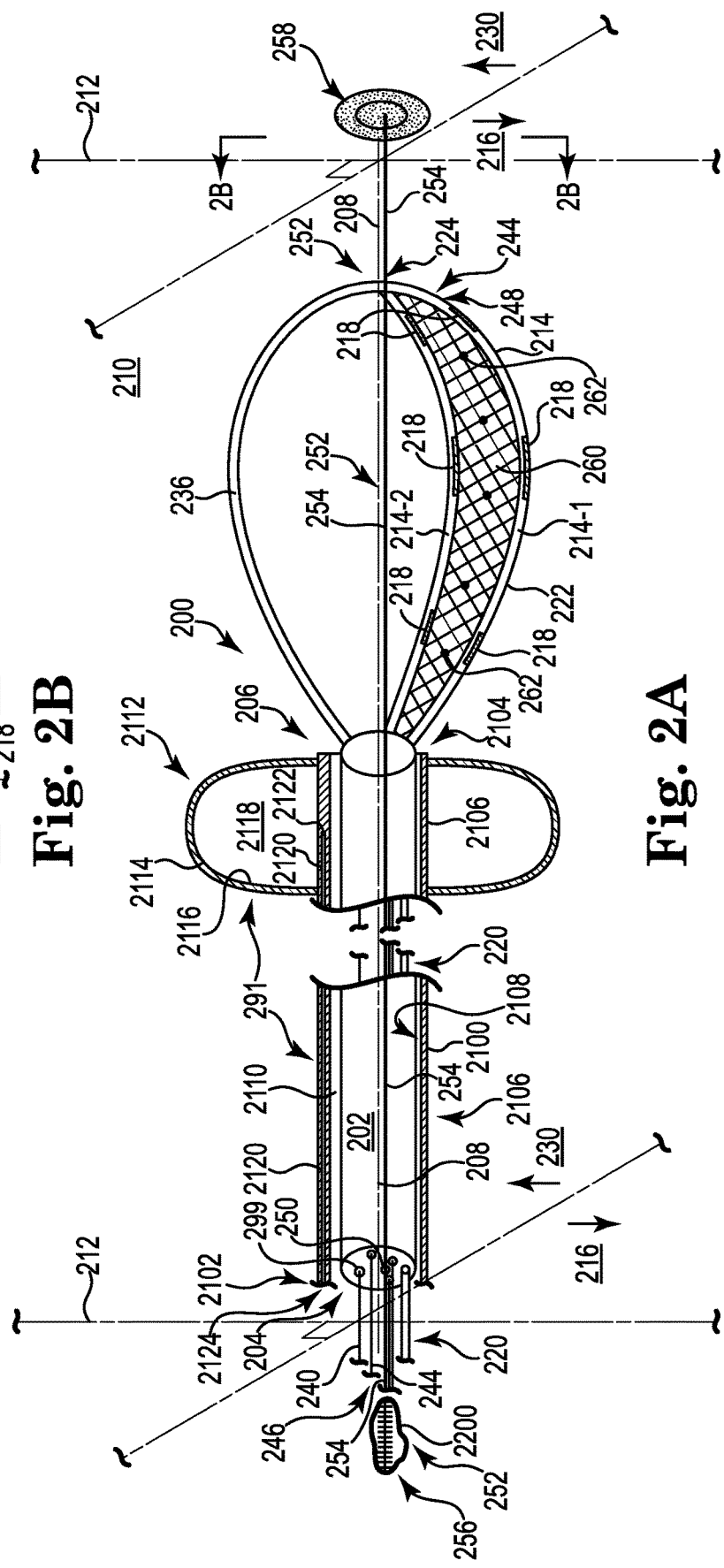
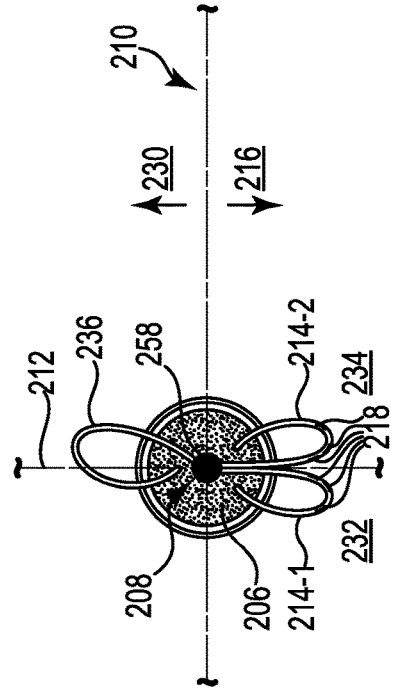
Fig. 2A
Fig. 2B

CATHETER AND CATHETER SYSTEM FOR ELECTRICAL NEUROMODULATION

TECHNICAL FIELD

The present disclosure relates generally to catheters and catheter systems, and more particularly to catheters and catheter systems for use in electrical neuromodulation.

BACKGROUND

Acute heart failure is a cardiac condition in which a problem with the structure or function of the heart impairs its ability to supply sufficient blood flow to meet the body's needs. The condition impairs quality of life and is a leading cause of hospitalizations and mortality in the western world. Treating acute heart failure is typically aimed at removal of precipitating causes, prevention of deterioration in cardiac function, and control of congestive state.

Treatments for acute heart failure include the use of inotropic agents, such as dopamine and dobutamine. These agents, however, have both chronotropic and inotropic effects and characteristically increase heart contractility at the expense of significant increments in oxygen consumption secondary to elevations in heart rate. As a result, although these inotropic agents increase myocardial contractility and improve hemodynamics, clinical trials have consistently demonstrated excess mortality caused by cardiac arrhythmias and increase in the myocardium consumption.

As such, there is a need for selectively and locally treating acute heart failure and otherwise achieving hemodynamic control without causing unwanted systemic effects.

SUMMARY

Embodiments of the present disclosure provide for a catheter and a catheter system for use in electrical neuromodulation. The catheter and the catheter system of the present disclosure, for example, may be useful in electrical neuromodulation of patients with cardiac disease, such as patients with chronic cardiac disease. As discussed herein, the configuration of the catheter and the catheter system of the present disclosure allows for a portion of the catheter to be positioned within the vasculature of the patient in the main pulmonary artery and/or one or both of the pulmonary arteries (the right pulmonary artery and the left pulmonary artery). Once positioned, the catheter and the catheter system of the present disclosure can provide electrical energy to stimulate the autonomic nerve fibers surrounding the main pulmonary artery and/or one or both of the pulmonary arteries in an effort to provide adjuvant cardiac therapy to the patient.

The catheter can include an elongate body having a first end and a second end. The elongate body includes an elongate radial axis that extends through the first end and the second end of the elongate body, and a first plane extends through the elongate radial axis. At least two elongate stimulation members extend from the elongate body, where each of the at least two elongate stimulation members curves into a first volume defined at least in part by the first plane. At least one electrode is on each of the at least two elongate stimulation members, where the at least one electrode form an electrode array in the first volume. Conductive elements extend through each of the elongate stimulation members, where the conductive elements conduct electrical current to combinations of two or more of the at least one electrode in the electrode array.

The at least two elongate stimulation members can curve only in the first volume defined at least in part by the first plane, and a second volume defined at least in part by the first plane and being opposite the first volume contains no electrodes. A second plane can perpendicularly intersect the first plane along the elongate radial axis of the elongate body to divide the first volume into a first quadrant volume and a second quadrant volume. The at least two elongate stimulation members can include a first elongate stimulation member and a second elongate stimulation member, where the first elongate stimulation member curves into the first quadrant volume and the second elongate stimulation member curves into the second quadrant volume.

Each of the at least two elongate stimulation members can include a stimulation member elongate body and a wire extending longitudinally through the elongate body and the stimulation member elongate body, where pressure applied by the wire against the stimulation member elongate body at or near its distal end causes the wire to deflect thereby imparting the curve into each of the at least two elongate stimulation members into the first volume defined at least in part by the first plane. The catheter can also include an anchor member that extends from the elongate body into a second volume defined at least in part by the first plane and opposite the first volume, where the anchor member does not include an electrode.

In an additional embodiment, the catheter can also include a structure extending between at least two of the least two elongate stimulation members. An additional electrode can be positioned on the structure, the additional electrode having a conductive element extending from the additional electrode through one of the elongate stimulation members, where the conductive element conducts electrical current to combinations of the additional electrode and at least one of the at least one electrode on each of the at least two elongate stimulation members. An example of such a structure is a mesh structure.

The catheter can also include a positioning gauge. The positioning gauge includes an elongate gauge body with a first end and a bumper end distal to the first end. The elongate body of the catheter includes a first lumen that extends from the first end through the second end of the elongate body. The bumper end has a shape with a surface area no less than a surface area of the distal end of the elongate body taken perpendicularly to the elongate radial axis, and the elongate gauge body extends through the first lumen of the elongate body to position the bumper end beyond the second end of the elongate body. The first end of the position gauge extends from the first end of the elongate body, the elongate gauge body having a marking that indicates a length between the second end of the elongate body and the bumper end of the position gauge.

The present disclosure also includes a catheter system that includes the catheter, as discussed herein, and a pulmonary artery catheter having a lumen, where the catheter extends through the lumen of the pulmonary artery catheter. The pulmonary artery catheter can include an elongate catheter body with a first end, a second end, a peripheral surface and an interior surface, opposite the peripheral surface, that defines the lumen extending between the first end and the second end of the elongate catheter body. An inflatable balloon is positioned on the peripheral surface of the elongate catheter body, the inflatable balloon having a balloon wall with an interior surface that along with a portion of the peripheral surface of the elongate catheter body defines a fluid tight volume. An inflation lumen extends through the elongate catheter body, the inflation lumen having a first opening into the fluid tight volume of the inflatable balloon and a second opening proximal to the first opening to allow for a fluid to move in the fluid tight volume to inflate and deflate the balloon.

The present disclosure also provides for a catheter that includes an elongate catheter body having a first end, a second end, a peripheral surface and an interior surface defining an inflation lumen that extends at least partially between the first end and the second end of the elongate catheter body; an inflatable balloon on the peripheral surface of the elongate catheter body, the inflatable balloon having a balloon wall with an interior surface that along with a portion of the peripheral surface of the elongate catheter body defines a fluid tight volume, where the inflation lumen has a first opening into the fluid tight volume of the inflatable balloon and a second opening proximal to the first opening to allow for a fluid to move in the volume to inflate and deflate the balloon; a plurality of electrodes positioned along the peripheral surface of the elongate catheter body, the plurality of electrodes located between the inflatable balloon and the first end of the elongate catheter body; conductive elements extending through the elongate catheter body, where the conductive elements conduct electrical current to combinations of two or more of the at least one electrode of the plurality of electrodes; and a first anchor extending laterally from the peripheral surface of the elongate body, the first anchor having struts forming an open framework with a peripheral surface having a largest outer dimension greater than a largest outer dimension of the inflatable balloon.

In one embodiment, the first anchor is positioned between the inflatable balloon and the plurality of electrodes positioned along the peripheral surface of the elongate catheter body. A portion of the elongate catheter body that includes the plurality of electrodes can curve in a predefined radial direction when placed under longitudinal compression. In another embodiment, the first anchor is positioned between the plurality of electrodes positioned along the peripheral surface of the elongate catheter body and the first end of the elongate catheter body.

The elongate catheter body can also include a second interior surface defining a shaping lumen that extends from the first end towards the second end. A shaping wire having a first end and a second end can pass through the shaping lumen with the first end of the shaping wire proximal to the first end of the elongate catheter body and the second end of the shaping wire joined to the elongate catheter body so that the shaping wire imparts a curve into a portion of the elongate catheter body having the plurality of electrodes when tension is applied to the shaping wire.

An embodiment of the catheter can also include an elongate catheter body having a first end, a second end, a peripheral surface and an interior surface defining an inflation lumen that extends at least partially between the first end and the second end of the elongate catheter body; an inflatable balloon on the peripheral surface of the elongate catheter body, the inflatable balloon having a balloon wall with an interior surface that along with a portion of the peripheral surface of the elongate catheter body defines a fluid tight volume, where the inflation lumen has a first opening into the fluid tight volume of the inflatable balloon and a second opening proximal to the first opening to allow for a fluid to move in the volume to inflate and deflate the balloon; a first anchor extending laterally from the peripheral surface of the elongate catheter body the first anchor having struts forming an open framework with a peripheral surface having a diameter larger than a diameter of the inflatable balloon; an electrode catheter having an electrode elongate body and a plurality of electrodes positioned along a peripheral surface of the electrode elongate body; conductive elements extending through the electrode elongate body of the electrode catheter, where the conductive elements conduct electrical current to combinations two or more of the at least one electrode of the plurality of electrodes; and an attachment ring joined to the electrode catheter and positioned around the peripheral surface of the elongate catheter body proximal to both the first anchor and the inflatable balloon.

A catheter system of the present disclosure can also include an elongate catheter body having a first end, a second end, a peripheral surface and an interior surface defining an inflation lumen that extends at least partially between the first end and the second end of the elongate catheter body, where the elongate catheter body includes an elongate radial axis that extends through the first end and the second end of the elongate body, and where a first plane extends through the elongate radial axis; an inflatable balloon on the peripheral surface of the elongate catheter body, the inflatable balloon having a balloon wall with an interior surface that along with a portion of the peripheral surface of the elongate catheter body defines a fluid tight volume, where the inflation lumen has a first opening into the fluid tight volume of the inflatable balloon and a second opening proximal to the first opening to allow for a fluid to move in the volume to inflate and deflate the balloon; an electrode cage having two or more of a rib that extend radially away from the peripheral surface of the elongate catheter body towards the inflatable balloon, where the two or more of the rib of the electrode cage curve into a first volume defined at least in part by the first plane; one or more electrodes on each of the rib of the electrode cage, where the one or more electrodes on each of the rib form an electrode array in the first volume; conductive elements extending through the two or more of the rib of the electrode cage and the elongate catheter body, where the conductive elements conduct electrical current to combinations of the one or more electrodes in the electrode array; and an anchoring cage having two or more of the rib that extend radially away from the peripheral surface of the elongate catheter body towards the inflatable balloon, where the two or more of the rib of the anchoring cage curve into a second volume defined at least in part by the first plane and being opposite the first volume, where the two or more of the rib of the anchoring cage do not include an electrode.

BRIEF DESCRIPTION OF THE FIGURES

FIG. 1A provides a profile view of a catheter according to an embodiment of the present disclosure.

FIG. 1B provides an end view of the catheter of FIG. 1A as viewed along lines 1B-1B in FIG. 1A.

FIG. 2A provides a profile view of a catheter according to an embodiment of the present disclosure.

FIG. 2B provides an end view of the catheter of FIG. 2A as viewed along lines 2B-2B in FIG. 2A.

DETAILED DESCRIPTION

Figure 3:
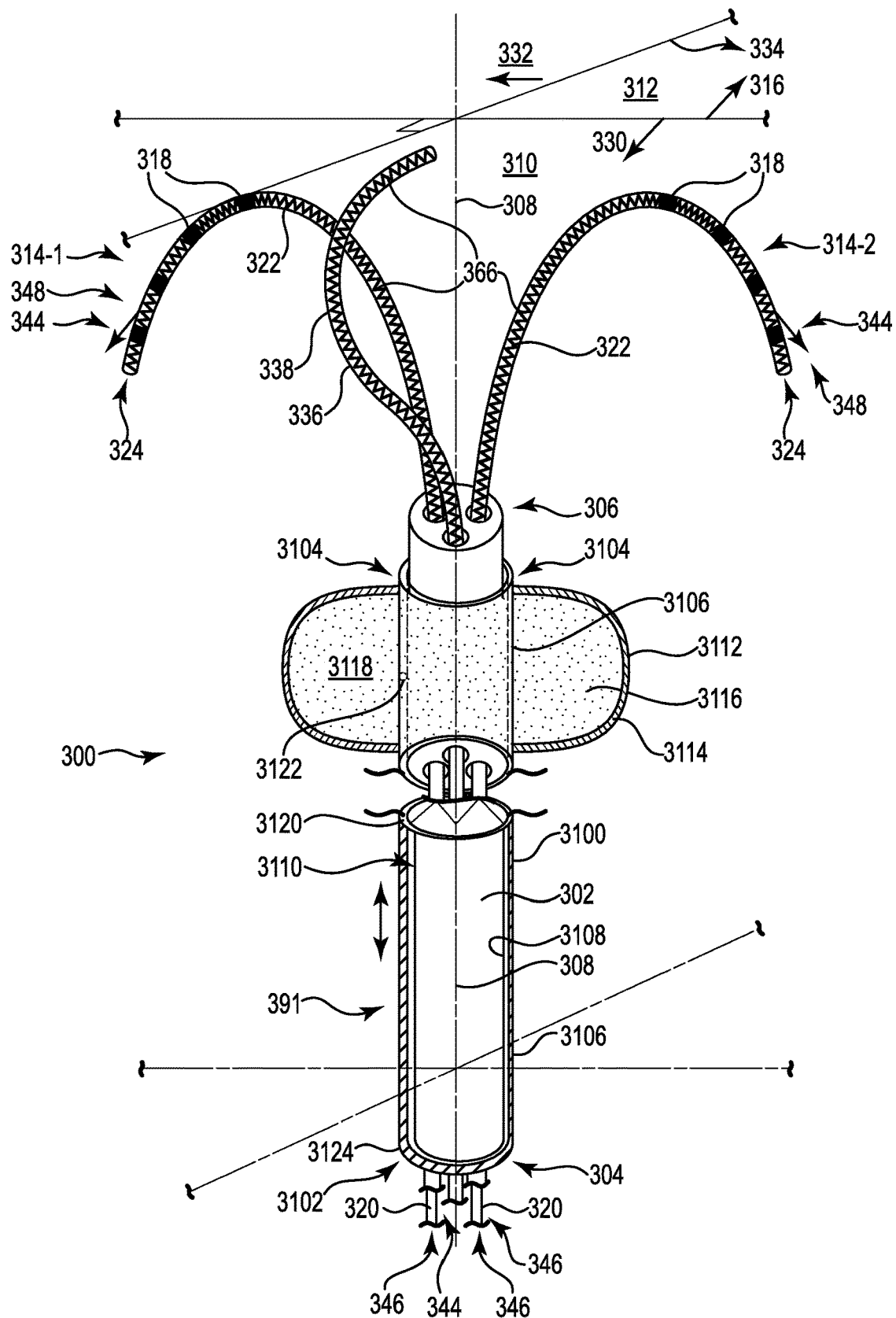
FIG. 3 illustrates a catheter according to an embodiment of the present disclosure.

Embodiments of the present disclosure provide for a catheter and a catheter system for use in electrical neuromodulation. The catheter and the catheter system of the present disclosure, for example, may be useful in electrical neuromodulation of patients with cardiac disease, such as patients with acute and/or chronic cardiac disease. As discussed herein, the configuration of the catheter and the catheter system of the present disclosure allows for a portion of the catheter to be positioned within the vasculature of the patient in the main pulmonary artery and/or one or both of the pulmonary arteries (the right pulmonary artery and the left pulmonary artery). Once positioned, the catheter and catheter system of the present disclosure can provide electrical energy to stimulate the autonomic nerve fibers surrounding the main pulmonary artery and/or one or both of the pulmonary arteries in an effort to provide adjuvant cardiac therapy to the patient.

The Figures herein follow a numbering convention in which the first digit or digits correspond to the drawing Figure number and the remaining digits identify an element or component in the drawing. Similar elements or components between different Figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of the present disclosure.

The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Referring to FIGS. 1A and 1B, there is shown a catheter 100 according to the present disclosure. FIG. 1A shows a side view of the catheter 100, while FIG. 1B shows an end view of the catheter 100 taken along view lines 1B-1B as seen in FIG. 1A. The catheter 100 includes an elongate body 102 having a first end 104 and a second end 106 distal from the first end 104. As illustrated, the elongate body 102 includes an elongate radial axis 108 that extends through the first end 104 and the second end 106 of the elongate body 102. As illustrated, a first plane 110 extends through the elongate radial axis 108 over the length of the elongate body 102. As used herein, a plane is an imaginary flat surface on which a straight line joining any two points on it would wholly lie and is used herein to help orientate the relative position of structures on the catheter 100. The first plane 110 is used herein, among other reasons, to help provide the relative position of electrodes that are located on the embodiments of the catheters provided herein. Catheter 100 further includes at least two elongate stimulation members 114 (as illustrated in FIGS. 1, 114-1 and 114-2). The stimulation members 114 extend from the elongate body 102, where each of the at least two elongate stimulation members 114-1 and 114-2 curves into a first volume 116 defined at least in part by the first plane 110. For example, the at least two elongate stimulation members 114 extend from approximately the second end 106 of the elongate body 102 into the first volume 116.

FIG. 1 also illustrates at least one electrode 118 on each of the at least two elongate stimulation members 114. The at least one electrode 118 on each of the elongate stimulation members 114 form an electrode array in the first volume 116 defined at least in part by the first plane 110. The at least one electrode 118 on each of the stimulation members 114 are electrically isolated from one another, where the stimulation members 114 are each formed of an electrically insulating material as discussed herein.

Each of the at least one electrode 118 is coupled to a corresponding conductive element 120. The conductive elements 120 are electrically isolated from each other and extend through the stimulation members 114 from each respective electrode 118 through the first end 104 of the elongate body 102. The conductive elements 120 terminate at a connector port, where each of the conductive elements 120 can be releasably coupled to a stimulation system, as discussed herein. It is also possible that the conductive elements 120 are permanently coupled to the stimulation system (e.g., not releasably coupled). The stimulation system can be used to provide stimulation electrical energy that is conducted through the conductive elements 120 and delivered across combinations of the electrodes 118 in the electrode array.

Each of the at least two elongate stimulation members 114 includes a stimulation member elongate body 122 having a distal end 124. As illustrated, the distal end 124 of the stimulation member elongate body 122 for each of the elongate stimulation members 114 extends from the elongate body 102. Each of the elongate body 102 and the stimulation member elongate body 122 include a surface defining a lumen 128 through which a wire 126 passes. The wire 126 is joined to its respective stimulation member elongate body 122 at or near the distal end 124, where the wire 126 then freely extends through the lumen 128 in the elongate stimulation member 114 past the first end 104 of the elongate body 102. The lumen 128 has a diameter that is large enough to allow the wire 126 to be moved longitudinally within the lumen 128. The portion of the wire 126 extending from the first end 104 can be used to apply pressure against the stimulation member elongate body 122 at or near the distal end 124, where the wire 126 under such pressure can deflect, or bend, thereby imparting the curve into each of the at least two elongate stimulation members 114 into the first volume 116 defined at least in part by the first plane 110. The at least two elongate stimulation members 114 extend radially away from the elongate body 102 over a range of distances depending upon how much pressure is applied to the wires

126. As illustrated, the curves of the at least two elongate stimulation members 114 can have a radius of curvature that changes along the length of the stimulation member elongate body 122.

As illustrated in FIGS. 1A and 1B, the at least two elongate stimulation members 114 curve only in the first volume 116 defined at least in part by the first plane 110. FIGS. 1A and 1B also illustrate a second volume 130 defined at least in part by the first plane 110 (being opposite the first volume 116) that contains no electrodes. FIGS. 1A and 1B also illustrate an embodiment in which the at least two elongate stimulation members 114 include a first elongate stimulation member 114-1 and a second elongate stimulation member 114-2. In addition to the first elongate stimulation member 114-1 and the second elongate stimulation member 114-2, FIGS. 1A and 1B show a second plane 112 perpendicularly intersecting the first plane 110 along the elongate radial axis 108 of the elongate body 102. The first plane 110 and the second plane 112 divide the first volume 116 into a first quadrant volume 132 and a second quadrant volume 134. As illustrated, the first elongate stimulation member 114-1 curves into the first quadrant volume 132, while the second elongate stimulation member 114-2 curves into the second quadrant volume 134.

The catheter 100 also includes an anchor member 136 that extends from the elongate body 102 into the second volume 130 defined at least in part by the first plane 110 and opposite the first volume 116. As illustrated, the anchor member 136 does not include an electrode. The anchor member 136 is not occlusive within the vasculature and/or does not encourage thrombosis or coagulation of the blood within the vasculature. The anchor member 136 and the elongate body 102 include surfaces defining a lumen 199 through which wire 140 passes. The wire 140 is joined to anchor member 136 at or near a distal end 197 of the member 136, where the wire 140 freely extends through the lumen 199 of the anchor member 136 past the first end 104 of the elongate body 102. The lumen 199 has a diameter that is large enough to allow the wire 140 to be moved longitudinally within the lumen 199. The portion of the wire 140 extending from the first end 104 can be used to apply pressure against the anchor member 136 at or near its distal end 197, where the wire 140 under such pressure can deflect, or bend, thereby imparting the curve into the anchor member 136. The anchor member 136 can extend radially away from the elongate body 102 over a range of distances depending upon how much pressure is applied to the wire 140. As discussed herein, the anchor member 136 can be used to bring the electrodes 118 into contact with a vascular lumenal surface (e.g., a posterior surface of the main pulmonary artery and/or one or both of the pulmonary arteries) with a variety of pressures. Optionally, the anchor member 136 can be configured to include one or more of the electrode 118, as discussed herein.

Each of the wires 126 and the wire 140, upon being used to impart the curves in their respective members, can then be releasably locked in place by preventing the longitudinal movement of the wire relative the elongate body 102. For example, a clamp or other device can be used to create contact between the wire and the surface of the lumen sufficient to prevent the wire from moving relative the surface of the lumen. This clamping action can also function as a hemostasis valve to minimize blood loss.

FIGS. 1A and 1B also illustrate a pulmonary artery catheter 191 (partially shown to show detail of catheter 100) that can be used with catheter 100 to provide for a catheter system. The pulmonary artery catheter 191 includes an elongate catheter body 1100 with a first end 1102, a second end 1104, a peripheral surface 1106 and an interior surface 1108, opposite the peripheral surface 1106. The interior surface 1108 defines a lumen 1110 that extends between the first end 1102 and the second end 1104 of the elongate catheter body 1100. The lumen 1110 is of a sufficient size and shape to house at least a portion of the catheter 100 inside the lumen 1110 during delivery of the catheter. For example, the anchor member 136 and the at least two elongate stimulation members 114, along with a least a portion of the elongate body 102, can be positioned within the lumen 1110. The anchor member 136, the at least two elongate stimulation members 114 and at least a portion of the elongate body 102 can be deployed from the distal end 1104 of the pulmonary artery catheter 191 during the delivery and implantation of the catheter 100.

The pulmonary artery catheter 191 can further include an inflatable balloon 1112 on the peripheral surface 1106 of the elongate catheter body 1100. The inflatable balloon 1112 has a balloon wall 1114 with an interior surface 1116 that along with a portion of the peripheral surface 1106 of the elongate catheter body 1100 defines a fluid tight volume 1118. The pulmonary artery catheter 191 further includes an inflation lumen 1120 that extends through the elongate catheter body 1100, where the inflation lumen 1118 has a first opening 1122 into the fluid tight volume 1116 of the inflatable balloon 1112 and a second opening 1124 proximal to the first opening 1122 to allow for a fluid to move in the fluid tight volume 1118 to inflate and deflate the balloon 1112. A syringe, or other known devices, containing the fluid (e.g., saline or a gas (e.g., oxygen)) can be used to inflate and deflate the balloon 1112. FIG. 1A shows the balloon 1112 in an inflated state, while FIG. 1B shows the balloon 1112 in a deflated state.

The catheter system shown in FIG. 1 can be used to position the catheter 100 in the main pulmonary artery and/or one or both of the pulmonary arteries of the patient, as described herein. To accomplish this, the pulmonary artery catheter 191 with the catheter 100 positioned within the lumen 1110 is introduced into the vasculature through a percutaneous incision, and guided to the right ventricle using known techniques. For example, the catheter 100 can be inserted into the vasculature via a peripheral vein of the arm (e.g., as with a peripherally inserted central catheter). Changes in a patient's electrocardiography and/or pressure signals from the vasculature can be used to guide and locate the catheter 100 within the patient's heart. Once in the proper location, the balloon 1112 can be inflated, as described, to allow the pulmonary artery catheter 191 and the catheter 100 to be carried by the flow of blood from the right ventricle to the main pulmonary artery and/or one of the pulmonary arteries. Additionally, various imaging modalities can be used in positioning the catheter and/or catheter system of the present disclosure in the main pulmonary artery and/or one of the pulmonary arteries of the patient. Such imaging modalities include, but are not limited to, fluoroscopy, ultrasound, electromagnetic, electropotential modalities.

The catheter system can be advance along the main pulmonary artery until the distal end 1104 of the pulmonary artery catheter 191 contacts the top of the main pulmonary artery (e.g., a location distal to the pulmonary valve and adjacent to both the pulmonary arteries). This can be done with the balloon 1112 in the inflated or deflated state. Once the distal end 1104 of the pulmonary artery catheter 191 reaches the top of the main pulmonary artery the elongate catheter body 1100 can be moved relative the catheter 100 so as to deploy the catheter 100 from the lumen 1110 of the pulmonary artery catheter 191.

Markings can be present on the peripheral surface of the catheter body 102, where the markings start and extend from the first end 104 towards the second end 106 of the catheter 100. The distance between the markings can be of units (e.g., millimeters, inches, etc.), which can allow the length between the distal end 1104 of the pulmonary artery catheter 191 and the top of the main pulmonary artery to be determined. A marking can also be provided on the peripheral surface of the catheter body 102 that indicates when the distal end 1104 of the pulmonary artery catheter 191 is clear of the anchor member 136 and the elongate stimulation members 114. In an alternative embodiment, a positioning gauge can be used to locate the catheter 100 within the main pulmonary artery, where the positioning gauge will be discussed herein in more detail.

The ability to measure this distance from the top of the main pulmonary artery may be helpful in placing the electrodes 118 in a desired location within the main pulmonary artery. In addition to measuring the distance from which the second end 106 of the elongate body 102 is placed from the top of the main pulmonary artery, the elongate body 102 can also be used to identify, or map, an optimal position for the electrodes 114 within the vasculature. For example, the second end 106 of the elongate body 102 can be positioned at the desired distance from the top of the main pulmonary artery using the markings on the peripheral surface of the catheter body 102. Wires 126 and 140 are then used to impart the curves into the elongate stimulation members 114 and the anchor member 136. Using both the wires 126 and the wire 140 the elongate stimulation members 114 and the anchor member 136 can be provided with curves of sufficient size to contact a surface of the main pulmonary artery, such as the anterior surface of the main pulmonary artery, and thereby bring the electrodes 118 into contact with the main pulmonary artery or one of the pulmonary arteries (the left pulmonary artery or the right pulmonary artery). The anchor member 136, as will be appreciated, biases and helps to anchor the electrodes 118 along the vessel surface (e.g., along the posterior surface of the main pulmonary artery or one of the pulmonary arteries (the left pulmonary artery or the right pulmonary artery)).

Due to its adjustable nature (e.g., how much pressure is applied to the wire 140), the anchor member 136 can be used to bring the electrodes 118 into contact with the lumenal surface of the main pulmonary artery or one of the pulmonary arteries with a variety of pressures. So, for example, the anchor member 136 can bring the electrodes 118 into contact with the lumenal surface of the main pulmonary artery or one of the pulmonary arteries with a first pressure. Using the stimulation system, as discussed herein, stimulation electrical energy can be delivered across combinations of two or more of the at least one electrode 118 in the electrode array. It is possible for the patient's cardiac response to the stimulation electrical energy to be monitored and recorded for comparison to other subsequent tests.

It is appreciated that for any of the catheters and/or catheter systems discussed herein any combination of electrodes, including reference electrodes (as discussed herein) positioned within or on the patient's body, can be used in providing stimulation to and sensing cardiac signals from the patient.

If necessary, the pressure can be reduced and the elongate body 102 can be rotated in either a clockwise or counter-clockwise direction to reposition the electrodes 118 in contact with the lumenal surface of the main pulmonary artery or one of the pulmonary arteries. The stimulation system can again be used to deliver stimulation electrical energy across combinations of two or more of the at least one electrode 118 in the electrode array. The patient's cardiac response to this subsequent test can then be monitored and recorded for comparison to previous and subsequent test. In this way, a preferred location for the position of the electrodes 118 along the lumenal surface of the main pulmonary artery or one of the pulmonary arteries can be identified. Once identified, the wire 140 can be used to increase the pressure applied by the anchor member 136, thereby helping to better anchor the catheter 100 in the patient.

Referring now to FIGS. 2A and 2B, there is shown an additional embodiment of catheter 200. FIG. 2A shows a side view of the catheter 200, while FIG. 2B shows an end view of the catheter 200 taken along view lines 2B-2B as seen in FIG. 2A. Catheter 200 includes at least the structures as discussed herein for catheter 100, a discussion of which is not repeated but the element numbers are included in FIGS. 2A and 2B with the understanding that the discussion of these elements is implicit.

In addition, catheter 200 further includes a structure 260 extending between at least two of the least two elongate stimulation members 214. The structure 260 is flexible such that it can transition between a delivery or low-profile state (radially folded state) that allows the structure 260 to be delivered into the main pulmonary artery and/or one of the pulmonary arteries, and a deployed or expanded state (radially expanded) as illustrated in FIG. 2A. As provided herein, the wires 226 and the least two elongate stimulation members 214 can be used to bring the structure 260 into its deployed or expanded state. As illustrated, an example of the structure 260 is a mesh structure.

The structure 260 has flexible strands that are connected to form a pattern of opening between the strands. Electrodes 262 can be present at one or more of the connections of the strands. The strands can be formed of the same insulative material as the elongate body 202 and the elongate stimulation members 214. Alternatively, a different insulative material than that used for the elongate body 202 and the elongate stimulation members 214 can be used for the strands of the structure 260. Examples of such insulative material for one or more portions of the catheters and structures provided herein can include, but are not limited to, medical grade polyurethanes, such as polyester-based polyurethanes, polyether-based polyurethanes, and polycarbonate-based polyurethanes; polyamides, polyamide block copolymers, polyolefins such as polyethylene (e.g., high density polyethylene); and polyimides, among others.

In addition to the shape provided by the elongate stimulation members 214, the structure 260 can also have a predefined shape that helps to locate and position the at least two of the least two elongate stimulation members 214 and the electrodes 218 thereon. So, for example, the structure 260 can be used to adjust and/or maintain the distance between electrodes 218 on the adjacent stimulation members 214.

The structure 260 can also include one or more of an additional electrode 262. The additional electrode 262 can either be positioned on the structure 260 or formed as an integral part of the structure 260, where each of the additional electrodes 262 is electrically isolated from each of the other electrodes 262 and/or 218. The additional electrode 262 includes a conductive element 264. Each of the conductive elements 264 are electrically isolated from each other and extend through the strands of the structure 260 from each respective additional electrode 262 through the stimulation members 214 and the elongate body 202 to the first end 204. The conductive elements 264 terminate at a connector port, where each of the conductive elements 220 and 264 can be releasably coupled to the stimulation system, as discussed herein. It is also possible that the conductive elements 120 are permanently coupled to the stimulation system (e.g., not releasably coupled). The stimulation system can be used to provide stimulation electrical energy that is conducted through the conductive elements 220 and 264 to combinations of the additional electrode 262 and at least one of the at least one electrode 218 on each of the at least two elongate stimulation members 214.

FIG. 2A also illustrates an anchor wire 244 extending longitudinally through the stimulation member elongate body 222. As illustrated, the elongate body 202 and the member elongate body 222 include a surface defining a lumen having a first opening at the proximal end 204 and a second opening at or adjacent to the distal end 224 of the stimulation member elongate body 222. The anchor wire 244 freely passes through the lumen, with a first end 246 extending from the elongate body 222 at the proximal end 204 of the elongate body 202 and a second end 248 having an anchoring structure (e.g., a barb) that extends from the second opening at or adjacent to the distal end 224 of the stimulation member elongate body 222. The anchor wire 244 can be advance through the lumen (e.g., longitudinal force can be applied to the first end 246 of the anchor wire 244) to extend the anchoring structure away from the stimulation member elongate body 214. In addition to the use of the anchor member 236 in helping to better anchor the catheter 200 in the patient, as discussed herein, the anchor wire 244 can also be used to help secure the catheter 200 in the patient at the desired location. One or more of the anchor wire and the associated structures can also be included with the catheter illustrated in FIGS. 1A and 1B. Optionally, the anchor wire 244 can be configured and used as an electrode with the stimulation system of the present disclosure.

FIG. 2 also illustrates a pulmonary artery catheter 291 (partially shown to show detail of catheter 200), as discussed herein.

As discussed herein, the catheter system shown in FIG. 2 can be used to position the catheter 200 in the main pulmonary artery and/or one of the pulmonary arteries of the patient, as described herein. To accomplish this, the pulmonary artery catheter 291 with the catheter 200 positioned within the lumen 2108 is introduced into the vasculature through a percutaneous incision, and guided to the right ventricle using known techniques. The balloon 2112 is inflated, as described, to allow the pulmonary artery catheter 291 and the catheter 200 to be carried by the flow of blood from the right ventricle to the main pulmonary artery or one of the pulmonary arteries.

The catheter system shown in FIGS. 2A and 2B illustrates an embodiment of the present disclosure that includes a positioning gauge 252. The positioning gauge 252 includes an elongate gauge body 254 with a first end 256 and a bumper end 258 distal to the first end 256. The elongate gauge body 254 can be moved longitudinally within a lumen 250 defined by a surface that extends through the elongate body 202 from its first end 204 through the second end 206. The bumper end 258 can have a shape with a surface area no less than a surface area of the distal end 206 of the elongate body 202 taken perpendicularly to the elongate radial axis 208. The elongate gauge body 254 extends through the first lumen 250 of the elongate body 202 to position the bumper end 258 beyond the second end 206 of the elongate body 202. The first end 256 of the position gauge 252 extends from the first end 204 of the elongate body 202, where the elongate gauge body 254 includes a marking 2200 that indicates a length between the second end 206 of the elongate body 202 and the bumper end 258 of the position gauge 252.

In deploying the catheter 200, the bumper end 258 of the positioning gauge 252 is approximately even with the distal end 224 of the stimulation member elongate body 222, the distal end 297 of the anchor member 236 and the distal end 2104 of the pulmonary artery catheter 291 (e.g., the elongate body 202, the anchor member 236 and the elongate stimulation members 214 are positioned within the lumen 2110 of the pulmonary artery catheter 291). In this configuration, the catheter system can be advance along the main pulmonary artery until the bumper end 258 of the positioning gauge 252 contacts the top of the main pulmonary artery (e.g., a location distal to the pulmonary valve and adjacent to both the pulmonary arteries). This can be done with the balloon 1112 in the inflated or deflated state.

Once the bumper end 258 contacts the top of the main pulmonary artery, the pulmonary artery catheter 291 (with the catheter 200 positioned within its lumen 2110) can be moved relative the bumper end 258 (e.g., the pulmonary artery catheter 291 and the catheter 200 are moved away from the bumper end 258). As the pulmonary artery catheter 291 and the catheter 200 move relative the bumper end 258 the markings 2200 on the elongate gauge body 254 can be used to indicate a length between the distal end 224 of the stimulation member elongate body 222/the distal end 297 of the anchor member 236/the distal end 2104 of the pulmonary artery catheter 291 and the bumper end 258 of the position gauge 252. As discussed herein, distance between the markings 2200 can be of units (e.g., millimeters, inches, etc.), which can allow the length from the between the distal end 224 of the stimulation member elongate body 222/the distal end 297 of the anchor member 236/the distal end 2104 of the pulmonary artery catheter 291 to be determined. Once a length that is desired is achieved, the pulmonary artery catheter 291 can be moved relative the catheter 200 so as to deploy the anchor member 236 and the elongate stimulation members 214 with the electrodes 218 within the main pulmonary artery or one of the pulmonary arteries.

As discussed herein, the ability to measure this distance from the top of the main pulmonary artery may be helpful in placing the electrodes 218 in a desired location within the main pulmonary artery or one of the pulmonary arteries. For example, the distal end 224 of the stimulation member elongate body 222 and the distal end 297 of the anchor member 236 can be positioned at the desired distance from the top of the main pulmonary artery using the markings on the peripheral surface of the positioning gauge 252. Wires 226 and 240 can be used to impart the curves into the elongate stimulation members 214 and the anchor member 236. Using both the wires 226 and the wire 240 the elongate stimulation members 214 and the anchor member 236 can be provided with curves of sufficient size to contact the anterior surface of the main pulmonary artery and thereby bring the electrodes 218 into contact with the lumenal surface of the main pulmonary artery. The anchor member 236, as will be appreciated, biases and helps to anchor the electrodes 218 along the vessel surface (e.g., along the posterior surface of the main pulmonary artery). Optionally, the anchor member 236 can be configured to include one or more of the electrode 218 as discussed herein.

Due to its adjustable nature (e.g., how much pressure is applied to the wire 240), the anchor member 236 can be used to bring the electrodes 218 into contact with the lumenal surface of the main pulmonary artery or one of the pulmonary arteries with a variety of pressures. So, for example, the anchor member 236 can bring the electrodes 218 into contact with the lumenal surface of the main pulmonary artery or one of the pulmonary arteries with a first pressure. Using stimulation electrical energy from the stimulation system, as discussed herein, of electrical energy can be delivered across combinations of two or more of the electrodes 218 in the electrode array. The patient's cardiac response to the stimulation electrical energy can then be monitored and recorded for comparison to other subsequent tests.

If necessary, the pressure can be reduced and the elongate body 202 can then be rotated in either a clockwise or counter-clockwise direction and/or lengthwise relative the top of the main pulmonary artery or one of the pulmonary arteries to reposition the electrodes 218 in contact with the lumenal surface of the main pulmonary artery or one of the pulmonary arteries. The stimulation system can again be used to deliver stimulation electrical energy across combinations of two or more of the electrodes 218 in the electrode array. The patient's cardiac response to this subsequent test can then be monitored and recorded for comparison to previous and subsequent test. In this way, a preferred location for the position of the electrodes 218 along the lumenal surface of the main pulmonary artery or one of the pulmonary arteries can be identified. Once identified, the wire 240 can be used to increase the pressure applied by the anchor member 236, thereby helping to better anchor the catheter 200 in the patient.

Referring now to FIG. 3, there is shown catheter 300, where catheter 300 includes the structures as discussed herein for catheters 100 and 200. As illustrated, catheter 300 includes an elongate body 302 having a first end 304 and a second end 306 distal from the first end 304. As illustrated, the elongate body 302 includes an elongate radial axis 308 that extends through the first end 304 and the second end 306 of the elongate body 302. As illustrated, a first plane 310 extends through the elongate radial axis 308 over the length of the elongate body 302. Catheter 300 further includes at least two elongate stimulation members 314, as discussed herein, that extend from the elongate body 302. Each of the at least two elongate stimulation members 314-1 and 314-2 curves into a first volume 316 defined at least in part by the first plane 310. For example, the at least two elongate stimulation members 314 extend from approximately the second end 306 of the elongate body 302 into the first volume 316.

FIG. 3 also illustrates at least one electrode 318 on each of the at least two elongate stimulation members 314. The electrodes 318 on the elongate stimulation members 314 form an electrode array on the first volume 316. The catheter 300 also includes conductive elements 320 that extend through each of the elongate stimulation members 314. As discussed herein, the conductive elements 320 can conduct electrical current to combinations of two or more of the electrodes 318.

Each of the at least two elongate stimulation members 314 includes a stimulation member elongate body 322 each having a distal end 324 that can move relative each other. In other words, the distal end 324 of each of the stimulation member elongate body 322 is free of each other. As illustrated in FIG. 3, the at least two elongate stimulation members 314 curve only in the first volume 316 defined at least in part by the first plane 310. FIG. 3 also illustrates a second volume 330 defined at least in part by the first plane 310 (being opposite the first volume 316) that contains no electrodes. FIG. 3 also illustrate an embodiment in which the at least two elongate stimulation members 314 include a first elongate stimulation member 314-1 and a second elongate stimulation member 314-2, where the first elongate stimulation member 314-1 curves into the first quadrant volume 332 and the second elongate stimulation member 314-2 curves into the second quadrant volume 334, as previously discussed herein. The catheter 300 also includes an anchor member 336 that extends from the elongate body 302 into the second volume 330. As illustrated, the anchor member 336 does not include an electrode. The anchor member 336 includes an elongate body 338 as previously discussed. Optionally, the anchor member 336 can be configured to include one or more of the electrode 318 as discussed herein.

Each of the at least two elongate stimulation members 314 and the anchor member 336 can also include a wire 366 extending longitudinally through the stimulation member elongate body 322 and the elongate body 338, respectively. The wire 366 can provide each of the at least two elongate stimulation members 314 and the anchor member 336 with a predefined shape. For example, the wire 366 in each of the at least two elongate stimulation members 314 and the anchor member 336 can have a coil or helical configuration that imparts a curve to the stimulation member elongate body 322 and the elongate body 338, respectively. The wire 366 can also impart stiffness to the stimulation member elongate body 322 that is sufficient to maintain the predefined shape under the conditions within the vasculature of the patient. So, for example, the wire 366 provides sufficient stiffness and flexibility to the stimulation member elongate body 322 to elastically return the least two elongate stimulation members 314 to their curved configuration when placed in the vasculature of a patient.

The wire 366 can be formed of a variety of metals or metal alloys. Examples of such metals or metal alloys include surgical grade stainless steel, such as austenitic 316 stainless among others, and the nickel and titanium alloy known as Nitinol. Other metals and/or metal alloys, as are known, can be used.

The at least two elongate stimulation members 314 can also include an anchor wire 344, as discussed herein, extending longitudinally through a lumen in the stimulation member elongate body 322 and the elongate body 302. The anchor wire 344 includes a first end 346 extending from the elongate body 302 and a second end 348 having an anchoring structure (e.g., a barb). The anchor wire 344 can be advance through the lumen (e.g, longitudinal force can be applied to the first end 346 of the anchor wire 344) to extend the anchoring structure away from the stimulation member elongate body 314. In addition to the use of the anchor member 336 in helping to better anchor the catheter 300 in the patient, as discussed herein, the anchor wire 344 can also be used to help secure the catheter 300 in the patient at the desired location. Optionally, the anchor wire 344 can be configured and used as an electrode with the stimulation system of the present disclosure.

The catheter 300 further includes a pulmonary artery catheter 391, as discussed herein. As illustrated, the pulmonary artery catheter 391 (partially shown to show detail of catheter 300) that can be used with catheter 300 to provide for a catheter system. The pulmonary artery catheter 391 includes an elongate catheter body 3100 with a first end 3102, a second end 3104, a peripheral surface 3106 and an interior surface 3108, opposite the peripheral surface 3106. The interior surface 3108 defines a lumen 3110 that extends between the first end 3102 and the second end 3104 of the elongate catheter body 3100. The lumen 3110 is of a sufficient size and shape to house at least a portion of the catheter 300 inside the lumen 3110 during delivery of the catheter. For example, the anchor member 336 and the at least two elongate stimulation members 314, along with a least a portion of the elongate body 302, can be positioned within the lumen 3110. The anchor member 336, the at least two elongate stimulation members 314 and at least a portion of the elongate body 302 can be deployed from the distal end 3104 of the pulmonary artery catheter 391 during the delivery and implantation of the catheter 300.

The pulmonary artery catheter 391 can further include an inflatable balloon 3112 on the peripheral surface 3106 of the elongate catheter body 3100. The inflatable balloon 3112 has a balloon wall 3114 with an interior surface 3116 that along with a portion of the peripheral surface 3106 of the elongate catheter body 3100 defines a fluid tight volume 3118. The pulmonary artery catheter 391 further includes an inflation lumen 3120 that extends through the elongate catheter body 3100, where the inflation lumen 3118 has a first opening 3122 into the fluid tight volume 3116 of the inflatable balloon 1112 and a second opening 3124 proximal to the first opening 3122 to allow for a fluid to move in the fluid tight volume 3118 to inflate and deflate the balloon 3112, as discussed herein. The catheter system shown in FIG. 3 can be used to position the catheter 300 in the main pulmonary artery and/or one or both of the pulmonary arteries of the patient, as described herein. The at least two elongate stimulation members 314 and the anchor member 336 can be repositioned within the lumen 3110 of the pulmonary artery catheter 391 by moving the elongate catheter body 3100 relative the elongate body 302 back over the at least two elongate stimulation members 314 and the anchor member 336.

The catheter system illustrated in FIG. 3 can optionally include the positioning gauge, as discussed herein.

For the various embodiments, the electrode can have a variety of configurations and sizes. For example, the electrodes discussed herein can be ring-electrodes that fully encircle the body on which they are located. The electrodes discussed herein can also be a partial ring, where the electrode only partially encircles the body on which they are located. For example, the electrodes can be partial ring electrodes that preferably only contact the lumenal surface of the main pulmonary artery and/or pulmonary arteries, as discussed herein. This configuration may help to localize the stimulation electrical energy, as discussed herein, into the vascular and adjacent tissue structures (e.g., autonomic fibers) and away from the blood. The electrodes and conductive elements provided herein can be formed of a conductive biocompatible metal or metal alloy. Examples of such conductive biocompatible metal or metal alloys include, but are not limited to, titanium, platinum or alloys thereof. Other biocompatible metal or metal alloys are known.

Figure 4:
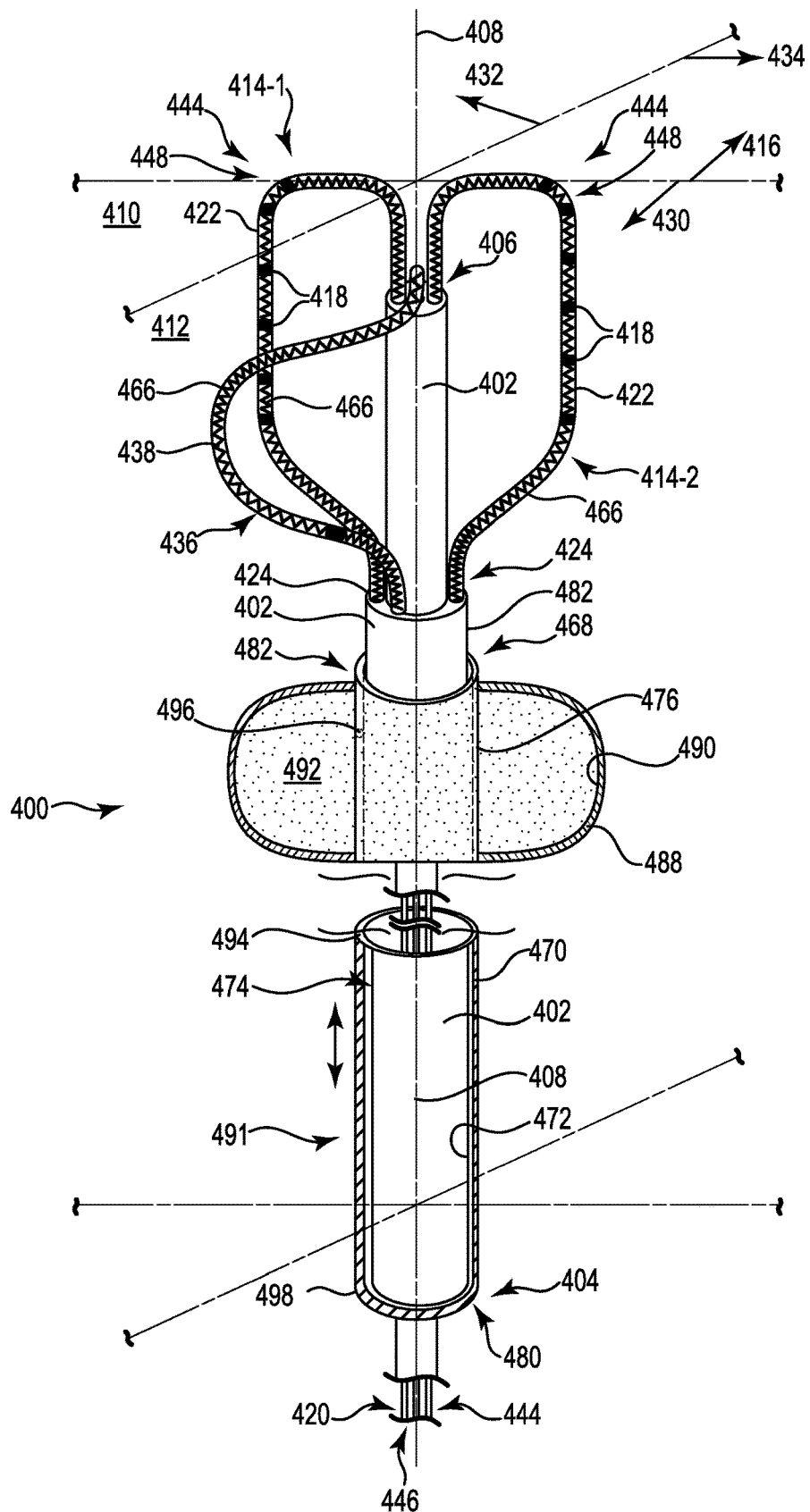
FIG. 4 illustrates a catheter according to an embodiment of the present disclosure.

Referring now to FIG. 4, there is shown catheter 400 according to the present disclosure. As illustrated, catheter 400 includes an elongate body 402 having a first end 404 and a second end 406 distal from the first end 404. As illustrated, the elongate body 402 includes an elongate radial axis 408 that extends through the first end 404 and the second end 406 of the elongate body 402. As illustrated, a first plane 410 extends through the elongate radial axis 408 over the length of the elongate body 402. Catheter 400 further includes at least two elongate stimulation members 414, as discussed herein, that extend from the elongate body 402. Each of the at least two elongate stimulation members 414-1 and 414-2 curves into a first volume 416 defined at least in part by the first plane 410. For example, the at least two elongate stimulation members 414 extend from approximately the second end 406 of the elongate body 402 into the first volume 416.

FIG. 4 also illustrates at least one electrode 418 on each of the at least two elongate stimulation members 414. The electrodes 418 on the elongate stimulation members 414 form an electrode array on the first volume 416. The catheter 400 also includes conductive elements 420 that extend through each of the elongate stimulation members 414. As discussed herein, the conductive elements 420 can conduct electrical current to combinations of two or more of the electrodes 418.

Each of the at least two elongate stimulation members 414 includes a stimulation member elongate body 422 each having a distal end 424 that extends from the elongate body 402. As illustrated in FIG. 4, the at least two elongate stimulation members 414 curve only in the first volume 416 defined at least in part by the first plane 410. FIG. 4 also illustrates a second volume 430 defined at least in part by the first plane 410 (being opposite the first volume 416) that contains no electrodes. FIG. 4 also illustrate an embodiment in which the at least two elongate stimulation members 414 include a first elongate stimulation member 414-1 and a second elongate stimulation member 414-2, where the first elongate stimulation member 414-1 curves into the first quadrant volume 432 and the second elongate stimulation member 414-2 curves into the second quadrant volume 434, as previously discussed herein. The catheter 400 also includes an anchor member 436 that extends from the elongate body 402 into the second volume 430. As illustrated, the anchor member 436 does not include an electrode. The anchor member 436 includes an elongate body 438 as previously discussed. Optionally, the anchor member 436 can be configured to include one or more of the electrode 418 as discussed herein.

Each of the at least two elongate stimulation members 414 and the anchor member 436 can also include a wire 466 extending longitudinally through the stimulation member elongate body 422 and the elongate body 438, respectively. The wire 466 can provide each of the at least two elongate stimulation members 414 and the anchor member 436 with a predefined shape. For example, the wire 466 in each of the at least two elongate stimulation members 414 and the anchor member 436 can have a coil or helical configuration that imparts a curve to the stimulation member elongate body 422 and the elongate body 438, respectively. The wire 466 can also impart stiffness to the stimulation member elongate body 422 that is sufficient to maintain the predefined shape under the conditions within the vasculature of the patient. So, for example, the wire 466 provides sufficient stiffness and flexibility to the stimulation member elongate body 422 to elastically return the least two elongate stimulation members 414 to their curved configuration when placed in the vasculature of a patient. The wire 466 can be formed of a variety of metals or metal alloys as discussed herein.

The at least two elongate stimulation members 414 can also include an anchor wire 444 extending longitudinally through the stimulation member elongate body 422. The anchor wire 444 includes a first end 446 extending from the elongate body 402 and a second end 448 having an anchoring structure (e.g., a barb). Longitudinal force applied to the first end 446 of the anchor wire 444 advances the anchor wire 444 through the stimulation member elongate body 414 to extend the anchoring structure away from the stimulation member elongate body 414. Optionally, the anchor wire 444 can be configured and used as an electrode with the stimulation system of the present disclosure.

The catheter 400 further includes a pulmonary artery catheter 491, as discussed herein. As illustrated, the pulmonary artery catheter 491 (partially shown to show detail of catheter 400) that can be used with catheter 400 to provide for a catheter system. The pulmonary artery catheter 491 includes an elongate catheter body 4100 with a first end 4102, a second end 4104, a peripheral surface 4106 and an interior surface 4108, opposite the peripheral surface 4106. The interior surface 4108 defines a lumen 4110 that extends between the first end 4102 and the second end 4104 of the elongate catheter body 4100. The lumen 4110 is of a sufficient size and shape to house at least a portion of the catheter 400 inside the lumen 4110 during delivery of the catheter. For example, the anchor member 436 and the at least two elongate stimulation members 414, along with a least a portion of the elongate body 402, can be positioned within the lumen 4110. The anchor member 436, the at least two elongate stimulation members 414 and at least a portion of the elongate body 402 can be deployed from the distal end 4104 of the pulmonary artery catheter 491 during the delivery and implantation of the catheter 400.

The pulmonary artery catheter 491 can further include an inflatable balloon 4112 on the peripheral surface 4106 of the elongate catheter body 4100. The inflatable balloon 4112 has a balloon wall 4114 with an interior surface 4116 that along with a portion of the peripheral surface 4106 of the elongate catheter body 4100 defines a fluid tight volume 4118. The pulmonary artery catheter 491 further includes an inflation lumen 4120 that extends through the elongate catheter body 4100, where the inflation lumen 4118 has a first opening 4122 into the fluid tight volume 4116 of the inflatable balloon 1112 and a second opening 4124 proximal to the first opening 4122 to allow for a fluid to move in the fluid tight volume 4118 to inflate and deflate the balloon 4112, as discussed herein. The catheter system shown in FIG. 4 can be used to position the catheter 400 in the main pulmonary artery and/or one or both of the pulmonary arteries of the patient, as described herein. The at least two elongate stimulation members 414 and the anchor member 436 can be repositioned within the lumen 4110 of the pulmonary artery catheter 491 by moving the elongate catheter body 4100 relative the elongate body 402 back over the at least two elongate stimulation members 414 and the anchor member 436.

The catheter system illustrated in FIG. 4 can optionally include the positioning gauge, as discussed herein.

Figure 5A:
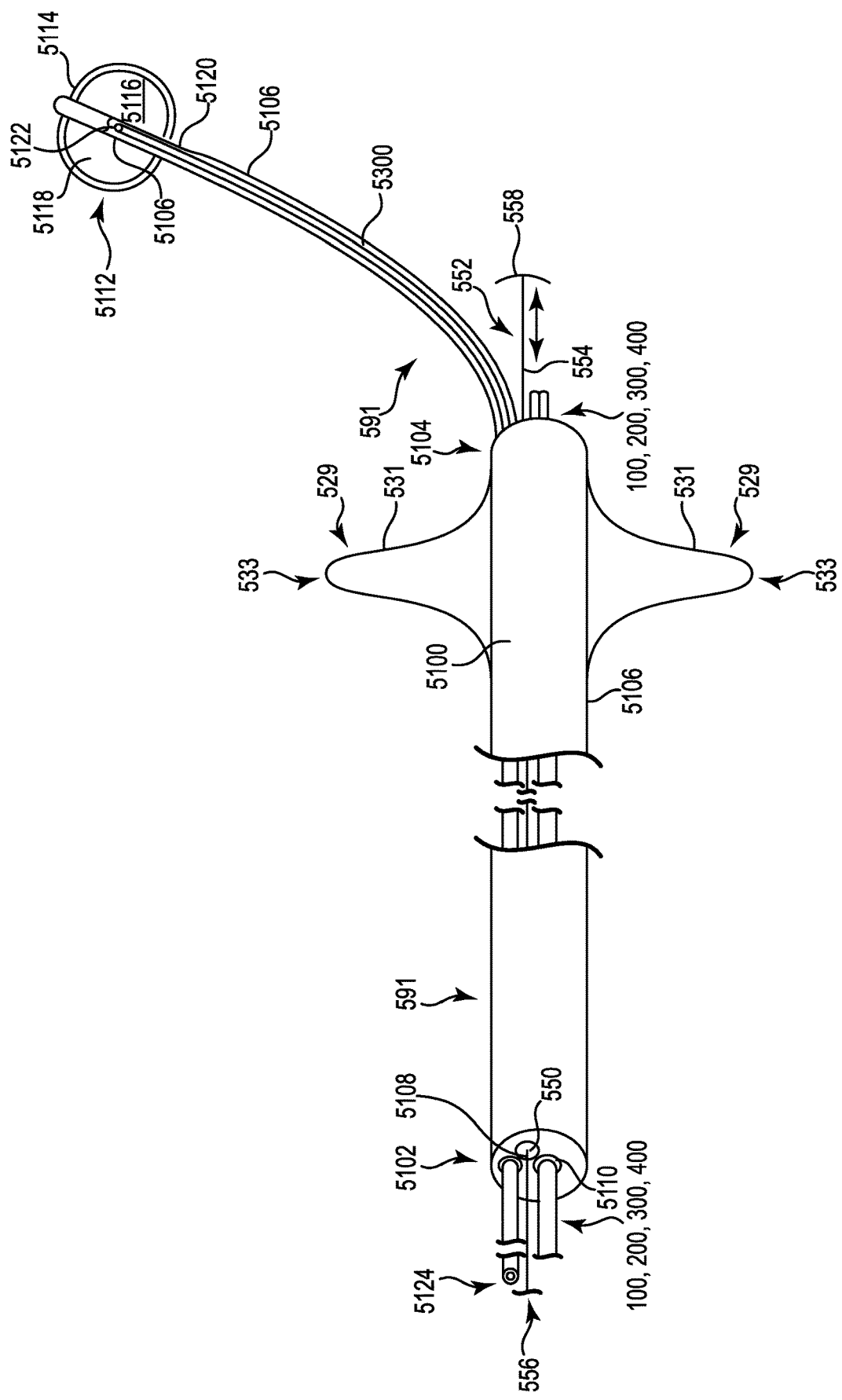
FIGS. 5A and 5B illustrate embodiments of a pulmonary artery catheter that can be used with the catheters according to the present disclosure.
Figure 5B:
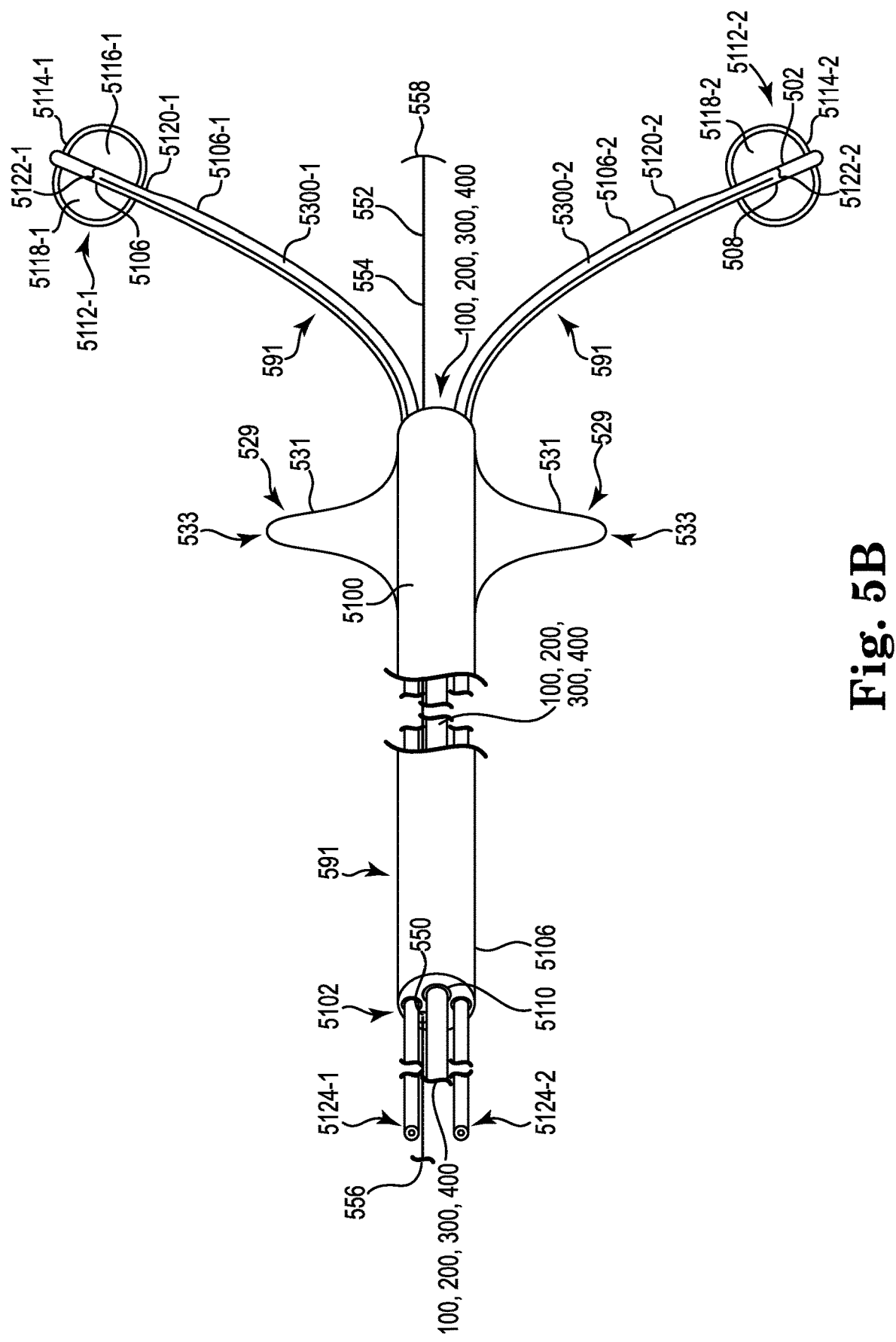

Referring now to FIGS. 5A and 5B, there is shown alternative embodiments of the pulmonary artery catheter 591 that can be used with the catheter (e.g., catheter 100, 200, 300 or 400) according to the present disclosure. As illustrated, the pulmonary artery catheter 591 includes an elongate catheter body 5100 with a first end 5102, a second end 5104, a peripheral surface 5106 and an interior surface 5108, opposite the peripheral surface 5106. The interior surface 5108 defines a lumen 5110 that extends between the first end 5102 and the second end 5104 of the elongate catheter body 5100. The lumen 5110 is of a sufficient size and shape to house at least a portion of the catheter 100, 200, 300 or 400 inside the lumen 5110 during delivery of the catheter. For example, the anchor member and the at least two elongate stimulation members, along with a least a portion of the elongate body, can be positioned within the lumen 5110. The anchor member, the at least two elongate stimulation members and at least a portion of the elongate body can be deployed from the distal end 5104 of the pulmonary artery catheter 591 during the delivery and implantation of the catheter 100, 200, 300 or 400.

The pulmonary artery catheter 591 includes an inflatable balloon 5112. As illustrated, the inflatable balloon 5112 is positioned on an elongate inflation catheter body 5300 that passes through a balloon lumen 5302. The balloon lumen 5302 is defined by lumen surface 5304 that can extend from the first end 5102 through the second end 5104 of the elongate catheter body 5100. The balloon lumen 5302 has a cross-sectional dimension that allows the elongate inflation catheter body 5300 to longitudinally move within the balloon lumen 5302. As such, the inflatable balloon 5112 can be moved relative the distal end 5104 of the pulmonary artery catheter 591.

The inflatable balloon 5112 has a balloon wall 5114 with an interior surface 5116 that along with a portion of a peripheral surface 5106 of the elongate inflation catheter body 5300 defines a fluid tight volume 5118. The elongate inflation catheter body 5300 further includes an inflation lumen 5120 that extends through the elongate inflation catheter body 5300, where the inflation lumen 5118 has a first opening 5122 into the fluid tight volume 5116 of the inflatable balloon 5112 and a second opening 5124 proximal to the first opening 5122 to allow for a fluid to move in the fluid tight volume 5118 to inflate and deflate the balloon 5112. A syringe, or other known devices, containing the fluid (e.g., saline or a gas (e.g., oxygen)) can be used to inflate and deflate the balloon 5112. The cross-sectional dimension of the balloon lumen 5302 is also sufficient to allow the inflatable balloon 5112 in its fully deflated state to be housed within the lumen 5302. The inflatable balloon 5112 along with at least a portion of the elongate inflation catheter body 5300 can be extended from the second end 5104 when the inflatable balloon 5112 is to be inflated.

FIG. 5B illustrates an alternative embodiment of the pulmonary artery catheter 591 that can be used with the catheter 100, 200, 300 or 400 according to the present disclosure. As with the pulmonary artery catheter 591 illustrated in FIG. 5A, the pulmonary artery catheter 591 includes the elongate catheter body 5100 with the first end 5102, the second end 5104, the peripheral surface 5106 and the interior surface 5108, opposite the peripheral surface 5106. The interior surface 5108 defines the lumen 5110 that extends between the first end 5102 and the second end 5104 of the elongate catheter body 5100. The lumen 5110 is of a sufficient size and shape to house at least a portion of the catheter 100, 200, 300 or 400 inside the lumen 5110 during delivery of the catheter. For example, the anchor member and the at least two elongate stimulation members, along with a least a portion of the elongate body, can be positioned within the lumen 5110 (the embodiment illustrated in FIG. 5B has the catheter 100, 200, 300 or 400 fully inside the lumen 5110). The anchor member, the at least two elongate stimulation members and at least a portion of the elongate body can be deployed from the distal end 5104 of the pulmonary artery catheter 591 during the delivery and implantation of the catheter 100, 200, 300 or 400.

The pulmonary artery catheter 591 illustrated in FIG. 5B also includes two of the inflatable balloons 5112 (shown as 5112-1 and 5112-2 in FIG. 5B). As illustrated, each of the inflatable balloons 5112-1 and 5112-2 are positioned on separate elongate inflation catheter bodies 5300-1 and 5300-2, where each of the elongate inflation catheter bodies 5300-1 and 5300-2 pass through a balloon lumen 5302-1 and 5302-2, respectively. As illustrated, each balloon lumen 5302-1 and 5302-2 is defined by a lumen surface 5304-1 and 5304-2, respectively, which can extend from the first end 5102 through the second end 5104 of the elongate catheter body 5100. The balloon lumen 5302-1 and 5302-2 each have a cross-sectional dimension that allows the elongate inflation catheter body 5300-1 and 5300-2 to longitudinally move within their respective balloon lumen 5302-1 and 5302-2. As such, each of the inflatable balloons 5112-1 and/or 5112-2 can be independently moved relative the distal end 5104 of the pulmonary artery catheter 591. As with FIG. 5A, the cross-sectional dimension of each balloon lumen 5302-1 and 5302-2 is sufficient to allow each respective inflatable balloon 5112-1 and 5112-2 in its fully deflated state to be housed within each respective lumen 5302-1 and 5302-2. Each inflatable balloon 5112-1 and 5112-2 along with at least a portion of the elongate inflation catheter body 5300-1 and 5300-2 can independently be extended from the second end 5104 when the inflatable balloon 5112-1 and/or 5112-2 is to be inflated.

Each of the inflatable balloons 5112-1 and 5112-2 has a balloon wall 5114-1 and 5114-2 with an interior surface 5116-1 and 5116-2, respectively, which along with a portion of a peripheral surface 5106 of the elongate inflation catheter body 5300-1 and 5300-2 define a fluid tight volume 5118-1 and 5118-2, respectively. The elongate inflation catheter body 5300 further includes an inflation lumen 5120-1 and 5120-2 that extends through the elongate inflation catheter body 5300-1 and 5300-2, respectively, where the inflation lumen 5118-1 has a first opening 5122 into the fluid tight volume 5116-1, 5116-2 of the inflatable balloon 5112-1 and 5112-2 and a second opening 5124-1 and 5124-2 proximal to the first opening 5122-1 and 5122-2 to allow for a fluid to move in the fluid tight volume 5118-1 and 5118-2 to inflate and deflate the balloon 5112-1 and 5112-2. Each of the inflatable balloons 5112-1 and 5112-2 can be independently moved relative the second end 5104 of the elongate body 5100 as well as independently inflated, as discussed herein.

The pulmonary artery catheter 591 further includes a positioning gauge 552. The positioning gauge 552 includes an elongate gauge body 554 with a first end 556 and a bumper end 558 distal to the first end 556. The elongate gauge body 554 can be moved longitudinally within a lumen 550 defined by a surface that extends through the elongate catheter body 5100. The elongate gauge body 554 extends through the first lumen 550 of the elongate catheter body 5100 to position the bumper end 558 beyond the second end 5104 of the elongate catheter body 5100. The first end 556 of the position gauge 552 extends from the first end 5102 of the elongate catheter body 5100, where the elongate gauge body 554 includes a marking 5200 that indicates a length between the second end 5104 of the elongate catheter body 5100 and the bumper end 558 of the position gauge 552.

The pulmonary artery catheter 591 can also include a first anchor 529 that extends laterally from the peripheral surface 5106 of the elongate catheter body 5100. As illustrated, the first anchor 529 has struts 531 that form an open framework. The struts 531 have a peripheral surface 533 having a largest outer dimension that allows the first anchor 529 when deployed to engage a surface of the main pulmonary artery and/or one or both of the pulmonary arteries. A sheath can cover and hold the first anchor 529 in an undeployed state as the pulmonary artery catheter 591 and the catheter 100, 200, 300, 400 are being introduced into the patient.

The catheter system shown in FIGS. 5A and 5B can be used to position the catheter 100, 200, 300 and/or 400 in the main pulmonary artery and/or one or both of the pulmonary arteries of the patient, as described herein. To accomplish this, the pulmonary artery catheter 591 with the catheter positioned within the lumen 5110 is introduced into the vasculature through a percutaneous incision, and guided to the right ventricle using known techniques. For the catheter system of FIG. 5A, the balloon 5112 is inflated, as described, to allow the pulmonary artery catheter 191 and the catheter 100 to be carried by the flow of blood from the right ventricle to the main pulmonary artery or one of the pulmonary arteries. Once the pulmonary artery catheter 591 and the catheter 100, 200, 300, 400 have been carried from the right ventricle into the main pulmonary artery or one of the pulmonary arteries the sheath can be retracted, allowing the first anchor 529 to deploy within the main pulmonary artery. The first anchor 529 can be brought back into its undeployed state by positioning the sheath (advancing the sheath) back over the first anchor 529.

With the first anchor 529 in its deployed position, the positioning gauge 552 can be used to determine a length between the second end 5104 of the elongate catheter body 5100 and the top of the main pulmonary artery (e.g., a location distal to the pulmonary valve and adjacent to both the pulmonary arteries). Knowing this length, the catheter 100, 200, 300, 400 can be advanced from the lumen 5110 of the elongate catheter body 5100 to a location between the second end 5104 of the elongate catheter body 5100 and the top of the main pulmonary artery. This location can be determined using markings (e.g., markings providing a length in, for example, millimeters) on a portion of the elongate body of the catheter 100, 200, 300, 400 that extends proximally from the first end 5102 of the elongate catheter body 5100. Referring now to FIGS. 6A through 6D, there is shown an additional embodiment of a catheter 600 according to the present disclosure. The catheter 600 includes an elongate catheter body 601 having a first end 603 and a second end 605. The elongate catheter body 601 also includes a peripheral surface 607 and an interior surface 609 defining an inflation lumen 611 (shown with a broken line) that extends at least partially between the first end 603 and the second end 605 of the elongate catheter body 601.

The catheter 600 includes an inflatable balloon 613 on the peripheral surface 607 of the elongate catheter body 601. The inflatable balloon 613 includes a balloon wall 615 with an interior surface 617 that along with a portion of the peripheral surface 607 of the elongate catheter body 601 defines a fluid tight volume 619. The inflation lumen 611 has a first opening 621 into the fluid tight volume 619 of the inflatable balloon 613 and a second opening 623 proximal to the first opening 621 to allow for a fluid to move in the volume 619 to inflate and deflate the balloon 613.

The catheter 600 further includes a plurality of electrodes 625 positioned along the peripheral surface 607 of the elongate catheter body 601. The plurality of electrodes 625 are located between the inflatable balloon 613 and the first end 603 of the elongate catheter body 601. Conductive elements 627 extend through the elongate catheter body 601, where the conductive elements 627 conduct electrical current to combinations of two or more of the at least one electrode of the plurality of electrodes 625.

The catheter 600 further includes a first anchor 629 that extends laterally from the peripheral surface 607 of the elongate body 601, the first anchor 629 having struts 631 forming an open framework. The struts 631 have a peripheral surface 633 having a largest outer dimension greater than the largest outer dimension of the inflatable balloon 613 (e.g., its largest diameter). As illustrated, the first anchor 629 has a center point 635 relative the peripheral surface 633 that is eccentric relative a center point 637 of the elongate catheter body 601 relative the peripheral surface 607.

Figure 6A:
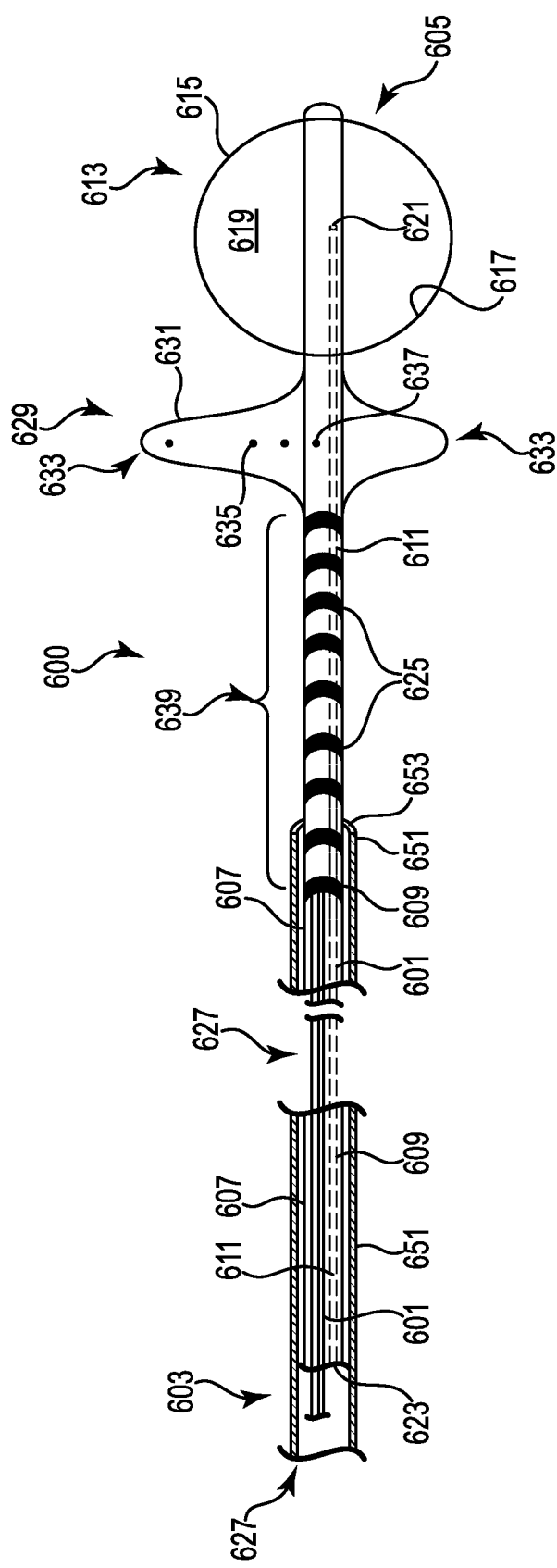
FIG. 6A illustrates a catheter according to an embodiment of the present disclosure.
Figure 6B:
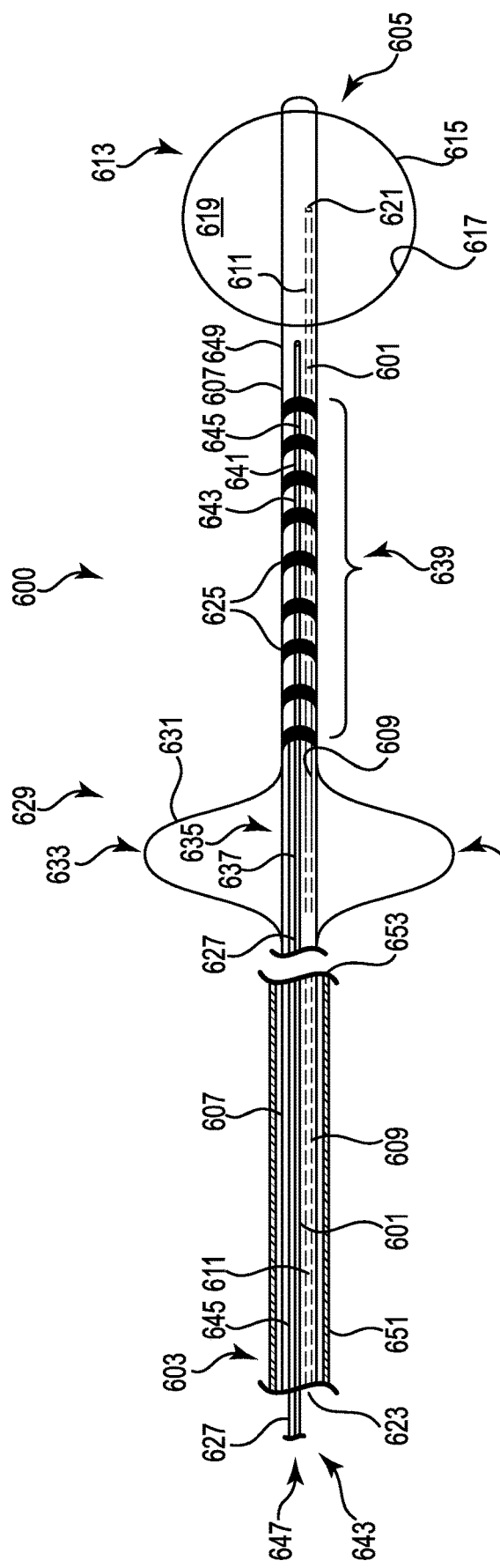
FIG. 6B illustrates a catheter according to an embodiment of the present disclosure.

FIGS. 6A and 6B both show the first anchor 629. FIG. 6A shows the first anchor 629 positioned between the inflatable balloon 613 and the plurality of electrodes 625 positioned along the peripheral surface 607 of the elongate catheter body 601. FIG. 6B shows the first anchor 629 positioned between the plurality of electrodes 625 positioned along the peripheral surface 607 of the elongate catheter body 601 and the first end 603 of the elongate catheter body 601.

For the catheter 600 shown in FIG. 6A, a portion 639 of the elongate catheter body 601 that includes the plurality of electrodes 625 curves in a predefined radial direction when placed under longitudinal compression. To provide this portion 639 that includes the plurality of electrodes 625, the elongate catheter body 601 can be pre-stressed and/or the wall can have thicknesses that allow for the elongate catheter body 601 to curve in the predefined radial direction when placed under longitudinal compression. In addition, or alternatively, structures such as coils or a helix of wire having different turns per unit length can be located within the elongate catheter body 601 in the portion 639. One or more of these structures can be used to allow the longitudinal compression to create the curve in the predefined radial direction in the portion 639. To achieve the longitudinal compression, the first anchor 629 can be deployed in the vasculature of the patient (e.g., in the pulmonary artery), where the first anchor 629 provides a location or point of resistance against the longitudinal movement of the elongate body 601. As such, this allows a compressive force to be generated in the elongate catheter body 601 sufficient to cause the portion 639 of the elongate catheter body 601 along which the plurality of electrodes 625 are present to curve in the predefined radial direction.

Figure 6C:
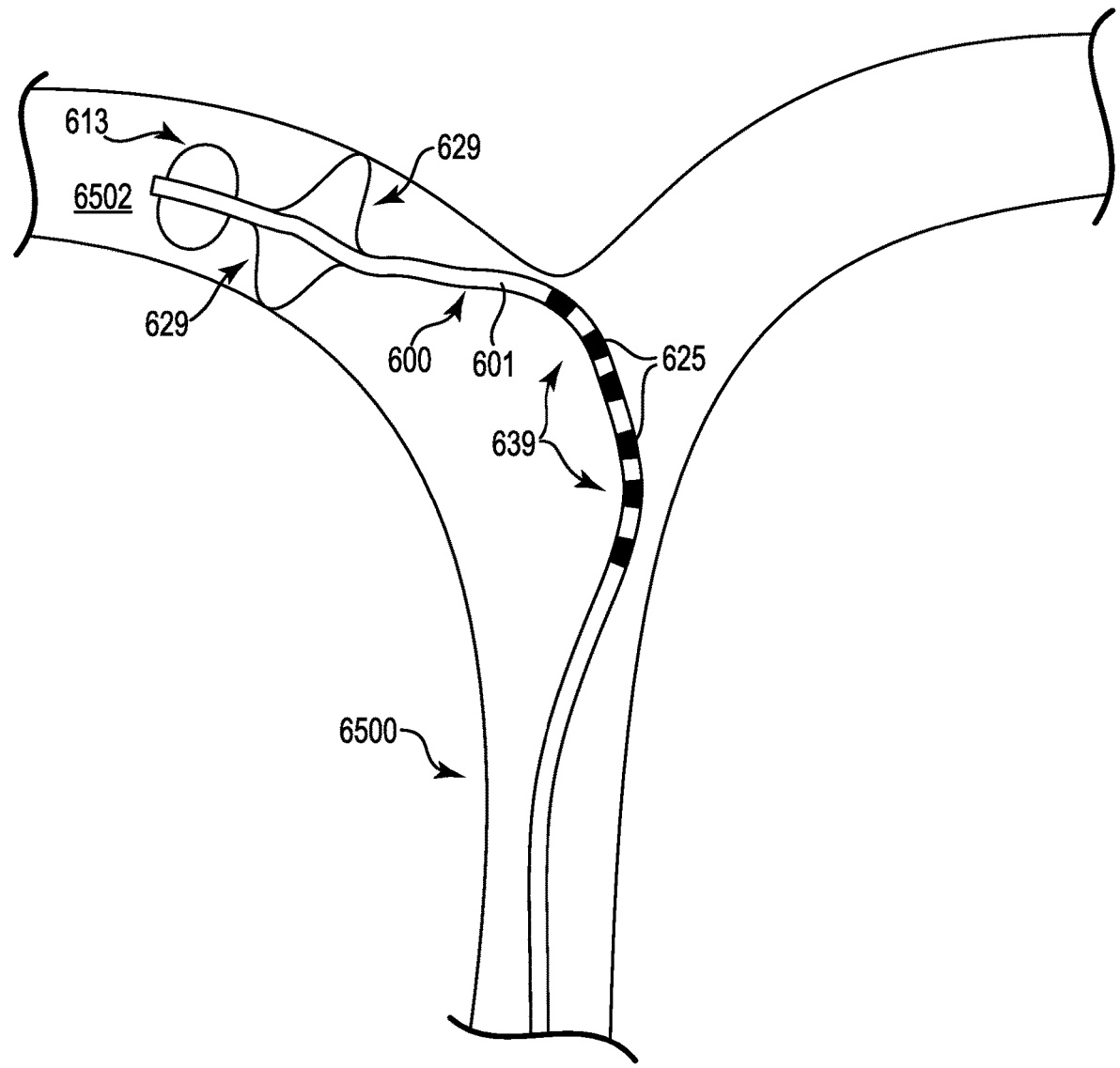
FIG. 6C illustrates the catheter provided in FIG. 6A positioned within the main pulmonary artery.

FIG. 6C provides an illustration of the portion 639 of the elongate catheter body 601 curved in a predefined radial direction when placed under longitudinal compression. The catheter 600 illustrated in FIG. 6C is shown in FIG. 6A and is described herein. As illustrated, the catheter 600 has been at least partially positioned within the main pulmonary artery 6500 of a patient's heart (the catheter 600 can also be at least partially positioned within the right pulmonary artery as illustrated), where the balloon 613 and the first anchor 629 are located in the lumen of the left pulmonary artery 6502. From this position, a compressive force applied to the elongate catheter body 601 can cause the portion 639 of the elongate catheter body 601 along which the plurality of electrodes 625 to curve in the predefined radial direction. This allows the plurality of electrodes 625 to extend towards and/or touch the lumenal surface of the main pulmonary artery. Preferably, the plurality of electrodes 625 are brought into position and/or contact with the lumenal surface of the main pulmonary artery.

Providing a rotational torque at the first end 603 of the elongate catheter body 601 can help to move the plurality of electrodes 625 relative the lumenal surface. This allows the professional to "sweep" the plurality of electrodes 625 into different positions along the lumenal surface of the main pulmonary artery. As discussed herein, this allows for the patient's cardiac response to the stimulation electrical energy to be monitored and recorded at a variety of locations along the lumenal surface of the pulmonary artery. In this way, a preferred location for the position of the electrodes 625 along the lumenal surface of the main pulmonary artery can be identified.

Figure 6D:
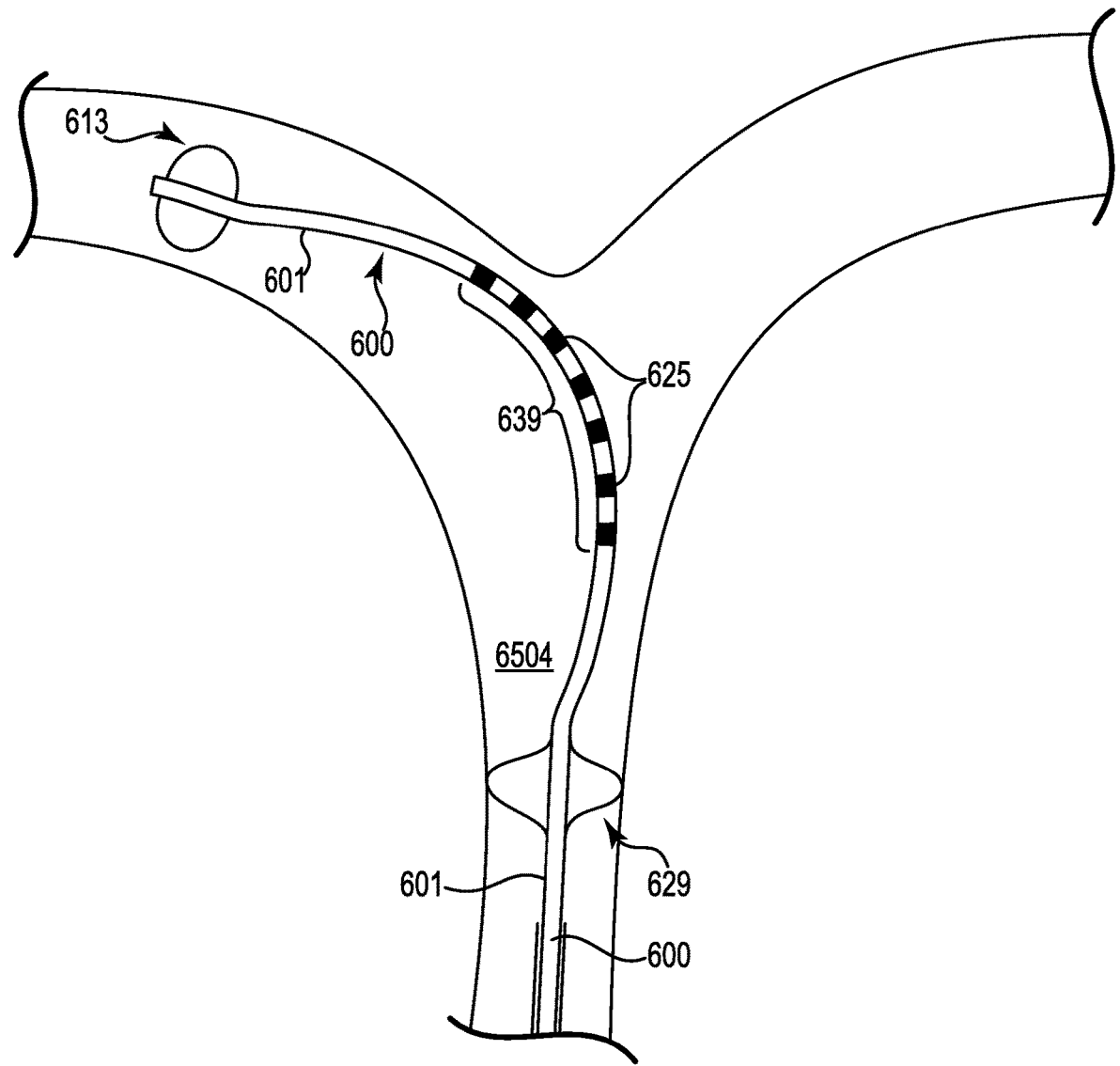
FIG. 6D illustrates the catheter provided in FIG. 6B positioned within the main pulmonary artery.

Alternatively, for the catheter 600 shown in FIG. 6B, the elongate catheter body 601 can include a second interior surface 641 defining a shaping lumen 643 that extends from the first end 603 towards the second end 605. The catheter 600 of FIG. 6B can also include a shaping wire 645 having a first end 647 and a second end 649. The shaping lumen 643 has a size (e.g., a diameter) sufficient to allow the shaping wire 645 to pass through the shaping lumen 643 with the first end 647 of the shaping wire 645 proximal to the first end 603 of the elongate catheter body 601 and the second end 649 of the shaping wire 645 joined to the elongate catheter body 601 so that the shaping wire 645 imparts a curve into the portion 639 of the elongate catheter body 601 having the plurality of electrodes 625 when tension is applied to the shaping wire 645. FIG. 6D provides an illustration of the portion 639 of the elongate catheter body 601 curved in a predefined radial direction when using the shaping lumen and shaping wire as discussed herein (the catheter 600 illustrated in FIG. 6D is shown in FIG. 6B and is described herein). As illustrated, the catheter 600 has been at least partially positioned within the main pulmonary artery 6500 of a patient's heart, where the balloon 613 is located in the lumen of the left pulmonary artery 6502 and the first anchor 629 is located in the main pulmonary artery 6504. From this position, the shaping wire can be used to impart the curve into the portion 639 of the elongate catheter body 601 having the plurality of electrodes 625 when tension is applied to the shaping wire 645. This allows the plurality of electrodes 625 to extend towards and/or touch the lumenal surface of the main pulmonary artery (the catheter 600 can also be at least partially positioned within the right pulmonary artery as illustrated). Preferably, the plurality of electrodes 625 are brought into position and/or contact with the lumenal surface of the main pulmonary artery.

Providing a rotational torque at the first end 603 of the elongate catheter body 601 can help to move the plurality of electrodes 625 relative the lumenal surface of the main pulmonary artery (and possibly the right or left pulmonary artery). This allows the professional to "sweep" the plurality of electrodes 625 into different positions along the lumenal surface of the main pulmonary artery, as discussed herein, so as to identify a preferred location for the position of the electrodes 625 along the lumenal surface of the main pulmonary artery.

The catheter 600 of FIGS. 6A and 6B both include an elongate delivery sheath 651 having a lumen 653 that extends over a peripheral surface 607 of the elongate body 601. The elongate delivery sheath 651, in a first position, can have the first anchor 629 positioned within the lumen 653 of the elongate delivery sheath 651. As the elongate delivery sheath 651 moves relative the peripheral surface 607 of the elongate body 601 the first anchor 629 extends from the peripheral surface 607 of the elongate body 601.

Figure 7:
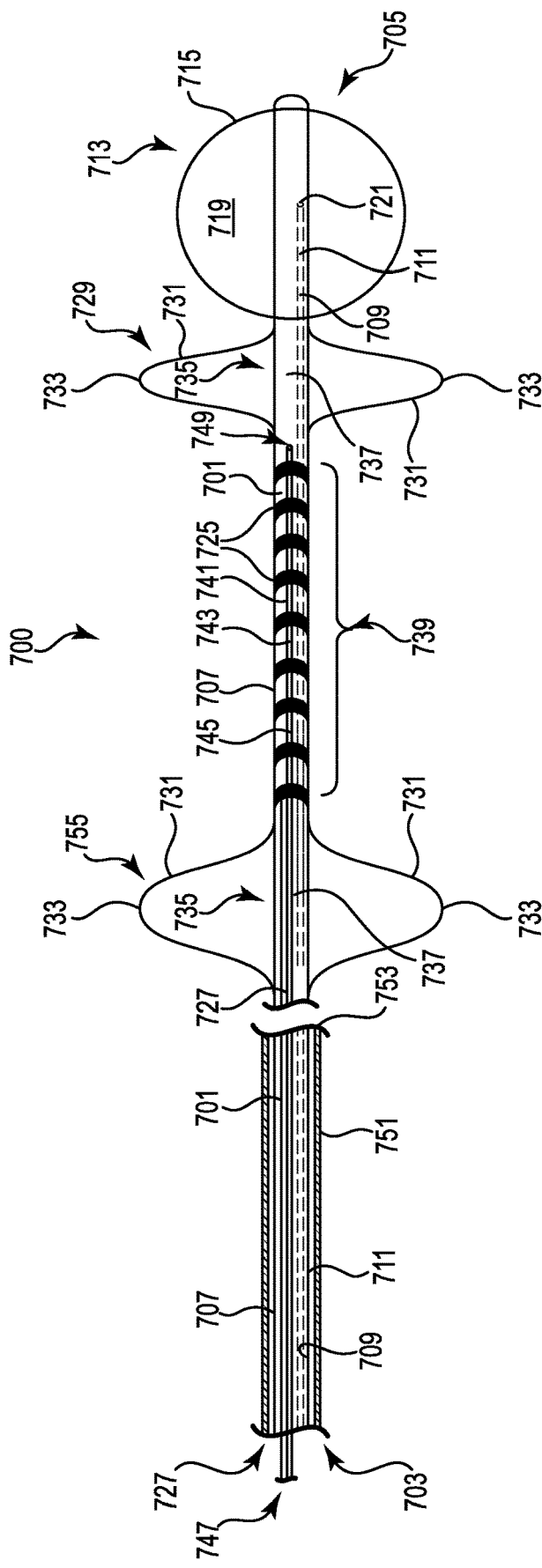
FIG. 7 illustrates a catheter according to an embodiment of the present disclosure.

Referring now to FIG. 7, there is shown an additional embodiment of a catheter 700 according to the present disclosure. As described for catheter 600, catheter 700 includes an elongate catheter body 701 having a first end 703 and a second end 705, a peripheral surface 707 and an interior surface 709 defining an inflation lumen 711 that extends at least partially between the first end 703 and the second end 705 of the elongate catheter body 701. Catheter 700 includes an inflatable balloon 713 on the peripheral surface 707 of the elongate catheter body 701, the inflatable balloon 713 having a balloon wall 715 with an interior surface 717 that along with a portion of the peripheral surface 707 of the elongate catheter body 701 defines a fluid tight volume 719. The inflation lumen 711 has a first opening 721 into the fluid tight volume 719 of the inflatable balloon 713 and a second opening 723 proximal to the first opening 721 to allow for a fluid to move in the volume 719 to inflate and deflate the balloon 713.

The catheter 700 includes a plurality of electrodes 725 positioned along the peripheral surface 707 of the elongate catheter body 701. The plurality of electrodes 725 are located between the inflatable balloon 713 and the first end 703 of the elongate catheter body 701. Conductive elements 727 extend through the elongate catheter body 701, where the conductive elements 727 conduct electrical current to combinations of two or more of the at least one electrode of the plurality of electrodes 725.

The catheter 700 further includes a first anchor 729 and a second anchor 755 that both extend laterally from the peripheral surface 707 of the elongate body 701. Both the first anchor 729 and the second anchor 755 have struts 731 that form an open framework for the anchors. The struts 731 have a peripheral surface 733 having a largest outer dimension greater than the largest outer dimension of the inflatable balloon 713 (e.g., its largest diameter). As illustrated, the first anchor 729 has a center point 735 relative the peripheral surface 733 that is eccentric relative a center point 737 of the elongate catheter body 701 relative the peripheral surface 707. In contrast, the second anchor 755 has a center point 735 relative the peripheral surface 733 that is concentric relative the center point 737 of the elongate catheter body 701 relative the peripheral surface 707.

The catheter 700 includes an elongate delivery sheath 751 having a lumen 753 that extends over a peripheral surface 707 of the elongate body 701. The elongate delivery sheath 751, in a first position, can have the first anchor 729 and the second anchor 755 positioned within the lumen 753 of the elongate delivery sheath 751. As the elongate delivery sheath 751 moves relative to the peripheral surface 707 of the elongate body 701 the first anchor 729 extends from the peripheral surface 707 of the elongate body 701. As the elongate delivery sheath 751 moves further away from the inflatable balloon 713 relative the peripheral surface 707 the second anchor 755 extends from the peripheral surface 707 of the elongate body 701.

As illustrated, the plurality of electrodes 725 are located between the first anchor 729 and the second anchor 755. A portion 739 of the elongate catheter body 701 that includes the plurality of electrodes 725 can be made to curve in a predefined radial direction in a variety of ways. For example, the portion 739 of the elongate catheter body 701 that includes the plurality of electrodes 725 can be made to curve in the predefined radial direction when placed under longitudinal compression (as discussed herein). As with catheter 600, to provide this portion 739 that includes the plurality of electrodes 725, the elongate catheter body 701 can be pre-stressed and/or the wall can have thicknesses that allow for the elongate catheter body 701 to curve in the predefined radial direction when placed under longitudinal compression. In addition, or alternatively, structures such as coils of a helix of wire having different turns per unit length can be located within the elongate catheter body 701 in the portion 739. One or more of these structures can be used to allow the longitudinal compression to create the curve in the predefined radial direction in the portion 739.

To achieve the longitudinal compression, the first anchor 729 can be deployed in the vasculature of the patient, as discussed herein, where the first anchor 729 provides a location or point of resistance against the longitudinal movement of the elongate body 701. As discussed herein, this can be accomplished by moving the elongate delivery sheath 751 relative the peripheral surface 707 of the elongate body 701 so as to allow the first anchor 729 to extend from the peripheral surface 707 of the elongate body 701. Once deployed, the first anchor 729 allows a compressive force to be generated in the elongate catheter body 701 sufficient to cause the portion 739 of the elongate catheter body 701 along which the plurality of electrodes 725 are present to curve in the predefined radial direction. Once the curve is formed in the predefined radial direction the elongate delivery sheath 751 is moved further away from the inflatable balloon 713 relative the peripheral surface 707 so as to allow the second anchor 755 to extend from the peripheral surface 707 of the elongate body 701.

Alternatively, the elongate catheter body 701 of the catheter 700 can include a second interior surface 741 defining a shaping lumen 743 that extends from the first end 703 towards the second end 705. The catheter 700 can also include a shaping wire 745 having a first end 747 and a second end 749, where the shaping lumen 743 has a size (e.g., a diameter) sufficient to allow the shaping wire 745 to pass through the shaping lumen 743 with the first end 747 of the shaping wire 745 proximal to the first end 703 of the elongate catheter body 701 and the second end 749 of the shaping wire 745 joined to the elongate catheter body 701 so that the shaping wire 745 imparts a curve into the portion 739 of the elongate catheter body 701 having the plurality of electrodes 725 when tension is applied to the shaping wire 745.

Figure 8:
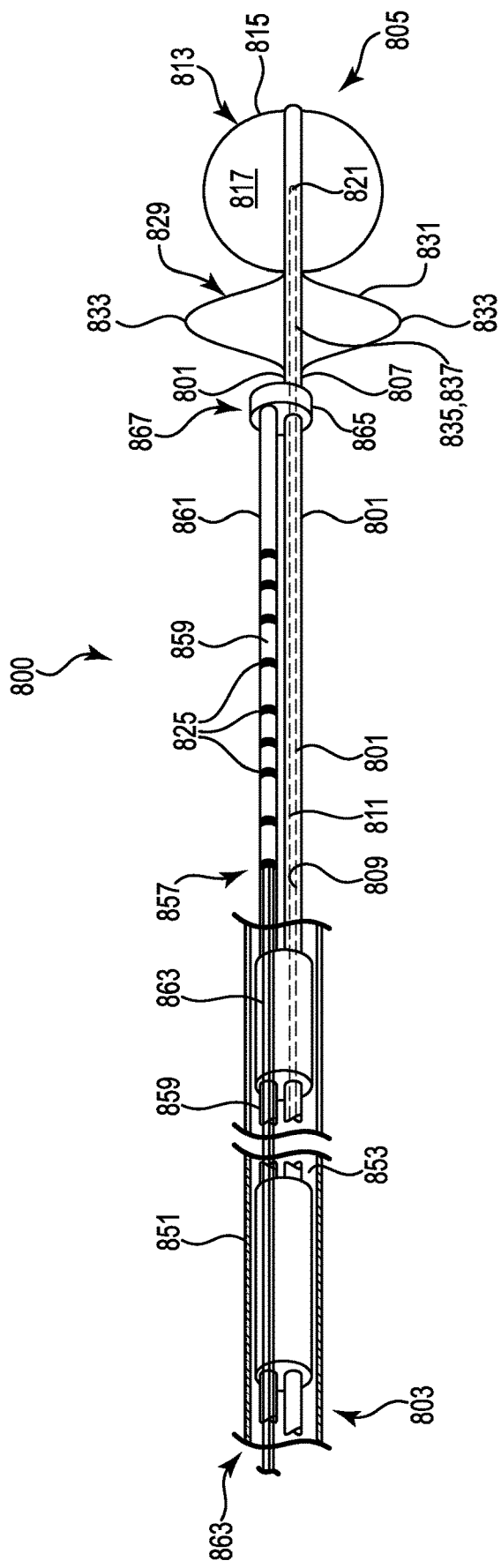
FIG. 8 illustrates a catheter according to an embodiment of the present disclosure.

Referring now to FIG. 8, there is shown an additional embodiment of the catheter 800. As discussed above, catheter 800 includes the elongate catheter body 801 having the first end 803, the second end 805, the peripheral surface 807 and the interior surface 809 defining the inflation lumen 811 that extends at least partially between the first end 803 and the second end 805 of the elongate catheter body 801. The catheter 800 also includes, as discussed herein, the inflatable balloon 813 on the peripheral surface 807 of the elongate catheter body 801, where the inflatable balloon 813 has the balloon wall 815 with the interior surface 817 that along with a portion of the peripheral surface 807 of the elongate catheter body 801 defines the fluid tight volume 819. The inflation lumen 811 has the first opening 821 into the fluid tight volume 819 of the inflatable balloon 815 and the second opening 823 proximal to the first opening 821 to allow for a fluid to move in the volume 819 to inflate and deflate the balloon 815.

The elongate catheter body 801 also includes a first anchor 829 that can extend laterally from the peripheral surface 807 of the elongate catheter body 801. As discussed herein, the first anchor 829 includes struts 831 forming an open framework with a peripheral surface 833 having a largest outer dimension greater than the largest outer dimension of the inflatable balloon 813 (e.g., its largest diameter). As illustrated, the first anchor 829 has a center point 835 relative the peripheral surface 833 that is eccentric relative a center point 837 of the elongate catheter body 801 relative the peripheral surface 807.

The catheter 800 further includes an electrode catheter 857 having an electrode elongate body 859 and a plurality of electrodes 825 positioned along a peripheral surface 861 of the electrode elongate body 859. Conductive elements 863 extend through the electrode elongate body 859 of the electrode catheter 857, where the conductive elements 863 conduct electrical current to combinations two or more of the at least one electrode of the plurality of electrodes 825. As illustrated, the first anchor 829 is positioned between the inflatable balloon 813 and the plurality of electrodes 825 positioned along the peripheral surface of the electrode elongate body 859.

The catheter 800 further includes an attachment ring 865 joined to the electrode catheter 857 and positioned around the peripheral surface 861 of the elongate catheter body 801 proximal to both the first anchor 829 and the inflatable balloon 813. The attachment ring 865 holds a distal end 867 of the electrode catheter 857 in a static relationship to the elongate catheter body 801. From this position the portion 839 of the electrode elongate body 859 that includes the plurality of electrodes 825 can be made to curve in a predefined radial direction, as previously discussed. The configuration of the portion 839 of the electrode elongate body 859 that includes the plurality of electrodes 825 that curves can be as discussed herein.

FIG. 8 also illustrates the elongate delivery sheath 851 having a lumen 853 that extends over the peripheral surface of the elongate catheter body 801 and the electrode catheter 857. The elongate delivery sheath 851, in a first position, can have the first anchor 829 positioned within the lumen 853 of the elongate delivery sheath 851. As the elongate delivery sheath 851 moves relative the peripheral surface 807 of the elongate body 801 and the peripheral surface 861 of the electrode catheter 857 the first anchor 829 extends from the peripheral surface 807 of the elongate body 801.

Figure 9:
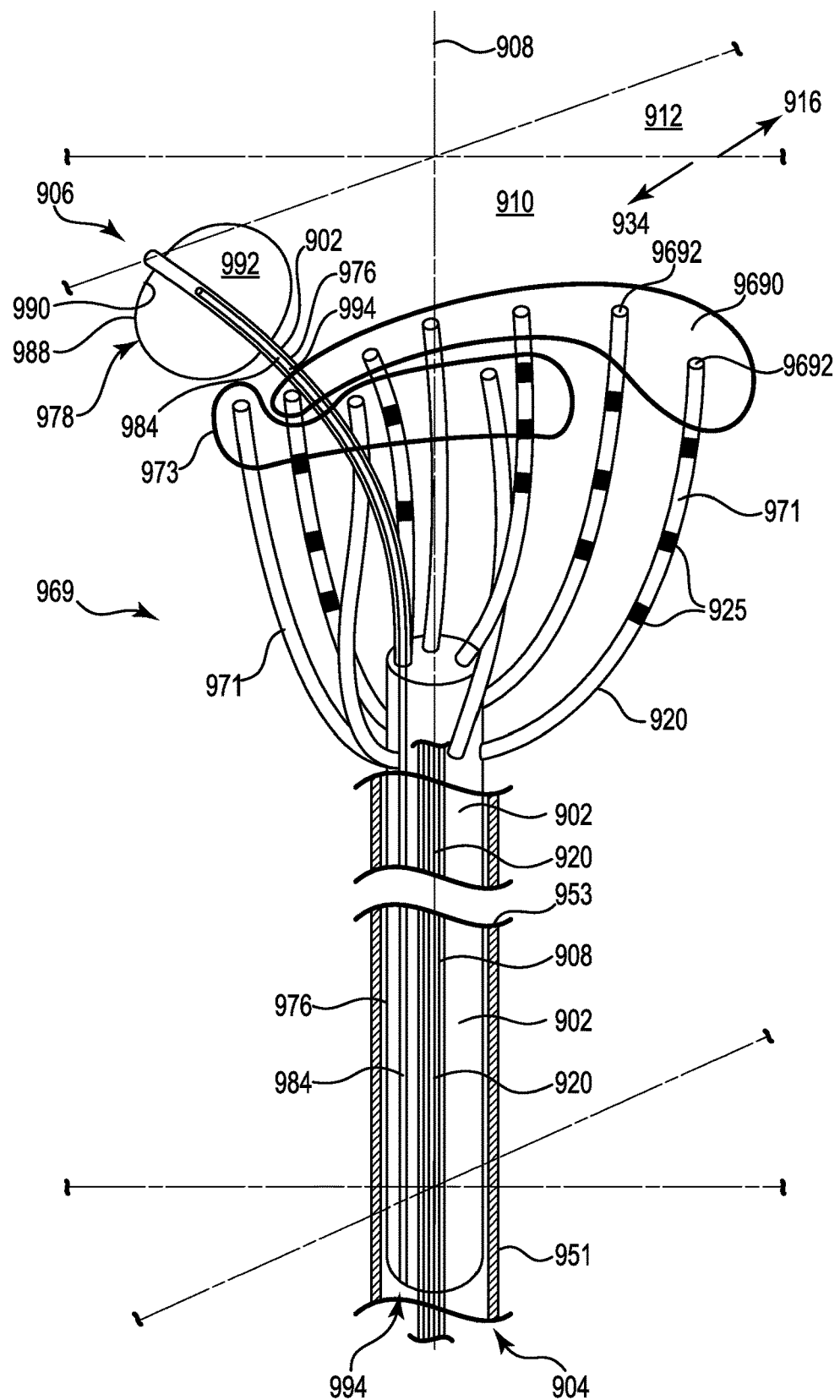
FIG. 9 illustrates a catheter system according to an embodiment of the present disclosure.

Referring now to FIG. 9, there is shown a catheter system 969. The catheter system 969 includes an elongate catheter body 902 having a first end 904, a second end 906, a peripheral surface 976 and an interior surface 984 defining an inflation lumen 994 that extends at least partially between the first end 904 and the second end 906 of the elongate catheter body 902. The elongate catheter body 902 includes a elongate radial axis 908 defined by an intersection of a first plane 910 and a second plane 912 perpendicular to the first plane 910, where the elongate radial axis 908 extends through the first end 904 and the second end 906 of the elongate catheter body 902.

The catheter system 969 further includes an inflatable balloon 978 on the peripheral surface 976 of the elongate catheter body 902. The inflatable balloon 978 has a balloon wall 988 with an interior surface 990 that along with a portion of the peripheral surface 976 of the elongate catheter body 902 defines a fluid tight volume 992. The inflation lumen 994 has a first opening 996 into the fluid tight volume 992 of the inflatable balloon 978 and a second opening 998 proximal to the first opening 996 to allow for a fluid to move in the volume 992 to inflate and deflate the balloon 978.

The catheter system 969 further includes an electrode cage 9690 having two or more of a rib 971 that extend radially away from the peripheral surface 976 of the elongate catheter body 902 towards the inflatable balloon 978. As illustrated, each of the two or more of the rib 971 of the electrode cage 9690 have a first end 9692 that extends away from the elongate catheter body 901 towards the inflatable balloon 978. Each of the first end 9692 of the two or more of the rib 971 of the electrode cage 9690 is free relative to every other first end of the two or more of the rib 971. In addition, the two or more of the rib 971 of the electrode cage 969 curve into a first half 916 of the first plane 910. Each of the ribs 971 of the electrode cage 969 also includes one or more electrodes 925. The one or more electrodes 925 on each of the rib 971 form an electrode array on the first half 916 of the first plane 910. The catheter system 969 further includes conductive elements 920 extending through the two or more of the rib 971 of the electrode cage 969 and the elongate catheter body 901, where the conductive elements 920 conduct electrical current to combinations of the two or more electrodes 925 in the electrode array.

The catheter system 969 also includes an anchoring cage 973 having two or more of the rib 971 that extend radially away from the peripheral surface 976 of the elongate catheter body 901 towards the inflatable balloon 978. As illustrated, the two or more of the rib 971 of the anchoring cage 973 curve into the second half 934 of the first plane 910, where the two or more of the rib 971 of the anchoring cage 973 do not include an electrode.

The catheter system 969 can further include a second inflatable balloon on the peripheral surface of the elongate catheter body. For example, the elongate catheter body can further include a third end and a second interior surface defining a second inflation lumen that extends at least partially between the first end and the third end of the elongate catheter body. The second inflatable balloon is located on the peripheral surface of the elongate catheter body adjacent the third end of the elongate catheter body. As with the first inflatable balloon, the second inflatable balloon includes a balloon wall with an interior surface that along with a portion of the peripheral surface of the elongate catheter body defines a fluid tight volume. The second inflation lumen has a first opening into the fluid tight volume of the second inflatable balloon and a second opening proximal to the first opening to allow for a fluid to move in the volume to inflate and deflate the second balloon.

FIG. 9 also illustrates the elongate delivery sheath 951 having a lumen 953 that extends over the peripheral surface of the elongate catheter body 901 and the ribs 971 of both the electrode cage 969 and the anchoring cage 973. The elongate delivery sheath 951, in a first position, can have the ribs 971 of both the electrode cage 969 and the anchoring cage 973 within the lumen 953 of the elongate delivery sheath 951. As the elongate delivery sheath 951 moves relative the peripheral surface 907 of the elongate body 901 the ribs 971 of the electrode cage 969 extend from the elongate body 901 to curve into the first half 916 of the first plane 910 and the ribs 971 of the anchoring cage 973 extend from the elongate body 901 to curve into the second half 934 of the first plane 910.

Each of the catheters and/or catheter systems discussed herein can further include one or more reference electrodes positioned proximal to the one or more electrodes present on the elongate body. These one or more reference electrodes each include insulated conductive leads that extend from the catheter and/or catheter system so as to allow the one or more reference electrodes to be used as common or return electrodes for electrical current that is delivered through one or more of the one or more electrodes on the elongate body of the catheter and/or catheter system.

The catheter and catheter systems of the present disclosure can be used to treat a patient with various cardiac conditions. Such cardiac conditions include, but are not limited to, acute heart failure, among others. As discussed herein, the one or more electrodes present on the catheter can be positioned within the main pulmonary artery and/or one or both of the pulmonary arteries. Preferably, the one or more electrodes are positioned in contact the lumenal surface of the main pulmonary artery (e.g., in physical contact with the surface of the posterior portion of the main pulmonary artery). As will be discussed herein, the one or more electrodes on the catheter and/or catheter system provided herein can be used to provide pulse of electrical energy between the electrodes and/or the reference electrodes. The electrodes of the present disclosure can be used in any one of a unipolar, bi-polar and/or a multi-polar configuration. Once positioned, the catheter and the catheter system of the present disclosure can provide the stimulation electrical energy to stimulate the nerve fibers (e.g., autonomic nerve fibers) surrounding the main pulmonary artery and/or one or both of the pulmonary arteries in an effort to provide adjuvant cardiac therapy to the patient (e.g., electrical cardiac neuromodulation).

In addition to the catheter and catheter system of the present disclosure, one or more sensing electrodes can be located on or within the patent. Among other things, the sensing electrodes can be used to detect signals indicting changes in various cardiac parameters, where these changes can be the result of the pulse of stimulation electrical energy delivered to stimulate the nerve fibers (e.g., autonomic nerve fibers) surrounding the main pulmonary artery and/or one or both of the pulmonary arteries. Such parameters include, but are not limited to, the patient's heart rate (e.g., pulse), among other parameters. The sensing electrodes can also provide signals indicting changes in one or more electrical parameter of vasculature (electrical activity of the cardiac cycle). Such signals can be collected and displayed, as are known, using known devices (e.g., electrocardiography (ECG) monitor) or a stimulation system, as discussed herein, which receives the detected signals and provides information about the patient.

Other sensors can also be used with the patient to detect and measure a variety of other signals indicting changes in various cardiac parameters. Such parameters can include, but are not limited to, blood pressure, blood oxygen level and/or gas composition of the patient's exhaled breath. For example, catheter and catheter system of the present disclosure can further include a pressure sensor positioned within or in-line with the inflation lumen for the inflatable balloon. Signals from the pressure sensor can be used to both detect and measure the blood pressure of the patient. Alternatively, the catheter and catheter system of the present disclosure can include an integrated circuit for sensing and measuring blood pressure and/or a blood oxygen level. Such an integrated circuit can be implemented using 0.18 µm CMOS technology. The oxygen sensor can be measured with optical or electrochemical techniques as are known. Examples of such oxygen sensors include reflectance or transmissive pulse oximetry those that use changes in absorbance in measured wavelengths optical sensor to help determined a blood oxygen level. For these various embodiments, the elongate body of the catheter can include the sensor (e.g., a blood oxygen sensor and/or a pressure sensor) and a conductive element, or elements, extending through each of the elongate body, where the conductive element conducts electrical signals from the blood oxygen sensor and/or the pressure sensor. The detected signals can also be used by the stimulation system to provide stimulation electrical energy in response to the detected signals. For example, one or more of these signals can be used by the stimulation system to deliver the stimulation electrical energy to the one or more electrodes of the catheter or catheter system. So, for example, detected signals from the patent's cardiac cycle (e.g., ECG waves, wave segments, wave intervals or complexes of the ECG waves) can be sensed using the sensing electrodes and/or timing parameter of the subject's blood pressure. The stimulation system can receive these detected signals and based on the features of the signal(s) generate and deliver the stimulation electrical energy to the one or more electrode of the catheter or catheter system. As discussed herein, the stimulation electrical energy is of sufficient current and potential along with a sufficient duration to stimulate one or more of the nerve fibers surrounding the main pulmonary artery and/or one or both of the pulmonary arteries so as to provide neuromodulation to the patient.

Figure 10:
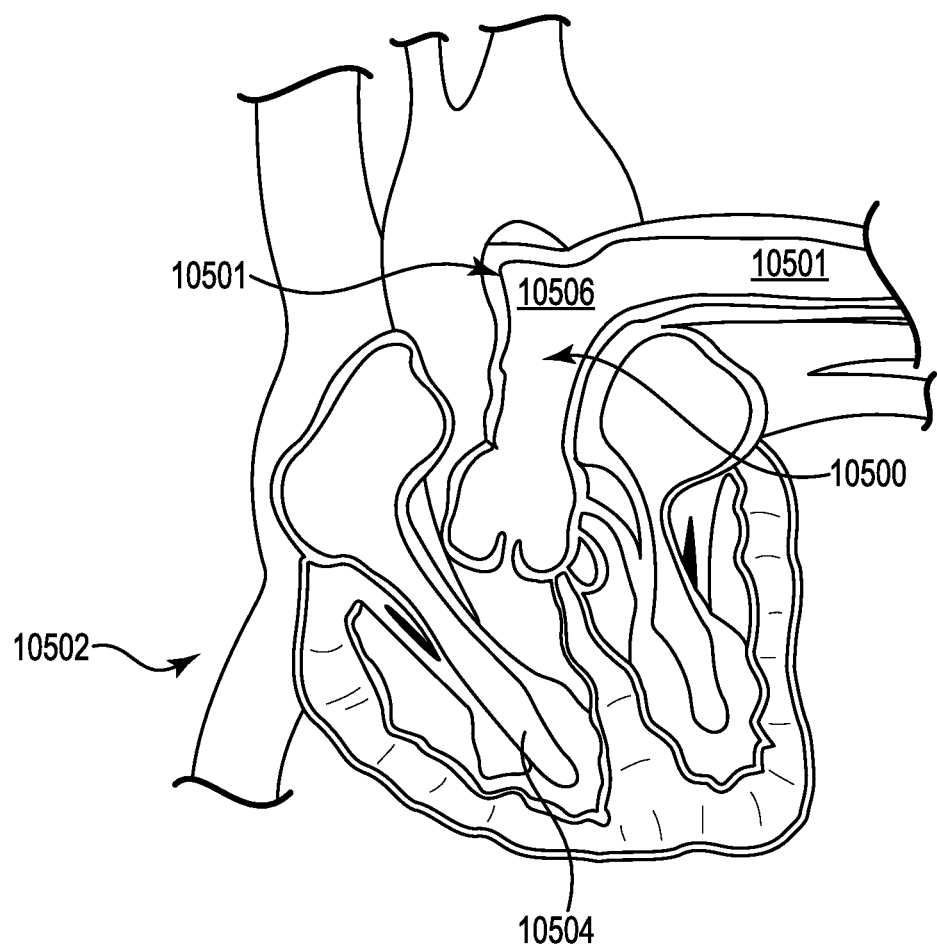
FIG. 10 provides an illustration of a main pulmonary artery of a heart.

Referring now to FIG. 10, there is shown an illustration of a main pulmonary artery 10500 of a heart 10502. The main pulmonary artery 10500 begins at the base of the right ventricle 10504, having a diameter of approximately 3 centimeter (1.2 in) and a length of about approximately 5 centimeters (2.0 in). The main pulmonary artery 10500 branches into two pulmonary arteries (left and right) 10501, which deliver deoxygenated blood to the corresponding lung. As illustrated, the main pulmonary artery 10500 has a posterior surface 10506 that arches over the left atrium and is adjacent the pulmonary vein. As discussed herein, the one or more electrodes of the catheter or catheter system of the present disclosure are positioned at least partially within the main pulmonary artery and/or a pulmonary artery with the electrode in contact with the posterior surface 10506. Other locations along the lumen of the main pulmonary artery and/or pulmonary arteries are also possible.

Preferably, the one or more electrodes of the catheter or catheter system of the present disclosure are in contact with the posterior surface 10506 of the main pulmonary artery 10500 and/or pulmonary arteries 10501. From this location, the stimulation electrical energy delivered through the one or more electrodes may be better able to treat and/or provide therapy (including adjuvant therapy) to the patient experiencing a variety of cardiovascular medical conditions, such as acute heart failure. The stimulation electrical energy can elicit responses from the autonomic nervous system that may help to modulate a patient's cardiac contractility. The stimulation electrical energy is intended to affect heart contractility more than the heart rate, thereby helping to improving hemodynamic control while possibly minimizing unwanted systemic effects.

As discussed herein, the catheter and/or catheter system of the present disclosure can be positioned in the pulmonary artery of the patient, where the one or more electrodes are positioned in contact the lumenal surface of the main pulmonary artery (e.g., in physical contact with the surface of the posterior portion of the main pulmonary artery). The stimulation system is electrically coupled to the one or more electrodes via the conductive elements, where the stimulation system can be used to deliver the stimulation electrical energy to the autonomic cardiopulmonary fibers surrounding the main pulmonary artery.

The stimulation system is used to operate and supply the stimulation electrical energy to the one or more electrodes of the catheter or catheter system. The stimulation system controls the various parameters of the stimulation electrical energy delivered across the one or more electrodes. Such parameters include control of each electrodes polarity (e.g., used as a cathode or an anode), pulsing mode (e.g., unipolar, bi-polar and/or multi-polar), a pulse width, an amplitude, a frequency, a voltage, a current, a duration, a wavelength and/or a waveform associated with the stimulation electrical energy. The stimulation system may operate and supply the stimulation electrical energy to different combinations and numbers of the one or more electrodes, including the reference electrodes discussed herein. The stimulation system can be external to the patient's body for use by the professional to program the stimulation system and to monitor its performance. Alternatively, the stimulation system could be internal to the patient's body. When located within the patient, the housing of the stimulation system can be used as a reference electrode for both sensing and unipolar pulsing mode.

As discussed herein, the stimulation system can be used to help identify a preferred location for the position of the one or more electrodes along the lumenal surface of the main pulmonary artery. To this end, the one or more electrodes of the catheter or catheter system are introduced into the patient and tests of various locations along the lumenal surface of the main pulmonary artery using the stimulation system are conducted so as to identify a preferred location for the electrodes, as discussed herein. During such a test, the stimulation system can be used to initiate and adjust the parameters of the stimulation electrical energy. Such parameters include, but are not limited to, terminating, increasing, decreasing, or changing the rate or pattern of the stimulation electrical energy. The stimulation system can also deliver stimulation electrical energy that are episodic, continuous, phasic, in clusters, intermittent, upon demand by the patient or medical personnel, or preprogrammed to respond to a signal, or portion of a signal, sensed from the patient.

By way of example, the stimulation electrical energy can have a voltage of about 0.1 microvolts to about 75 volts (V), where voltage values of 1 V to 50 V, or 0.1 V to 10 V are also possible. The stimulation electrical energy can be delivered at a frequency of about 1 Hertz (Hz) to about 100,000 Hz, where frequency values of about 2 Hz to about 200 Hz are also possible. The stimulation electrical energy can have a pulse width of about 100 microseconds to about 100 milliseconds. The stimulation electrical energy can also have a variety of wave forms, such as for example, square wave, biphasic square wave, sine wave, or other electrically safe and feasible combinations. The stimulation electrical energy may be applied to multiple target sites simultaneously or sequentially.

An open-loop or closed-loop feedback mechanism may be used in conjunction with the present disclosure. For the open-loop feedback mechanism, a professional can monitor cardiac parameters and changes to the cardiac parameters of the patient. Based on the cardiac parameters the professional can adjust the parameters of the stimulation electrical energy applied to autonomic cardiopulmonary fibers. Non-limiting examples of cardiac parameters monitored include arterial blood pressure, central venous pressure, capillary pressure, systolic pressure variation, arterial blood gases, cardiac output, systemic vascular resistance, pulmonary artery wedge pressure, gas composition of the patient's exhaled breath and/or mixed venous oxygen saturation. Cardiac parameters can be monitored by an electrocardiogram, invasive hemodynamics, an echocardiogram, or blood pressure measurement or other devices known in the art to measure cardiac function. Other parameters such as body temperature and respiratory rate can also be monitored and processed as part of the feedback mechanism.

In a closed-loop feedback mechanism, the cardiac parameters of the patient are received and processed by the stimulation system, as discussed herein, where the parameters of the stimulation electrical energy are adjusted based at least in part on the cardiac parameters. As discussed herein, a sensor is used to detect a cardiac parameter and generate a sensor signal. The sensor signal is processed by a sensor signal processor, which provides a control signal to a signal generator. The signal generator, in turn, can generate a response to the control signal by activating or adjusting one or more of the parameters of the stimulation electrical energy applied by the catheter or catheter system to the patient. The control signal can initiate, terminate, increase, decrease or change the parameters of the stimulation electrical energy. It is possible for the one or more electrodes of the catheter or catheter system to be used as a sensor a recording electrode. When necessary these sensing or recording electrodes may delivery stimulation therapy as discussed herein.

Figure 11:
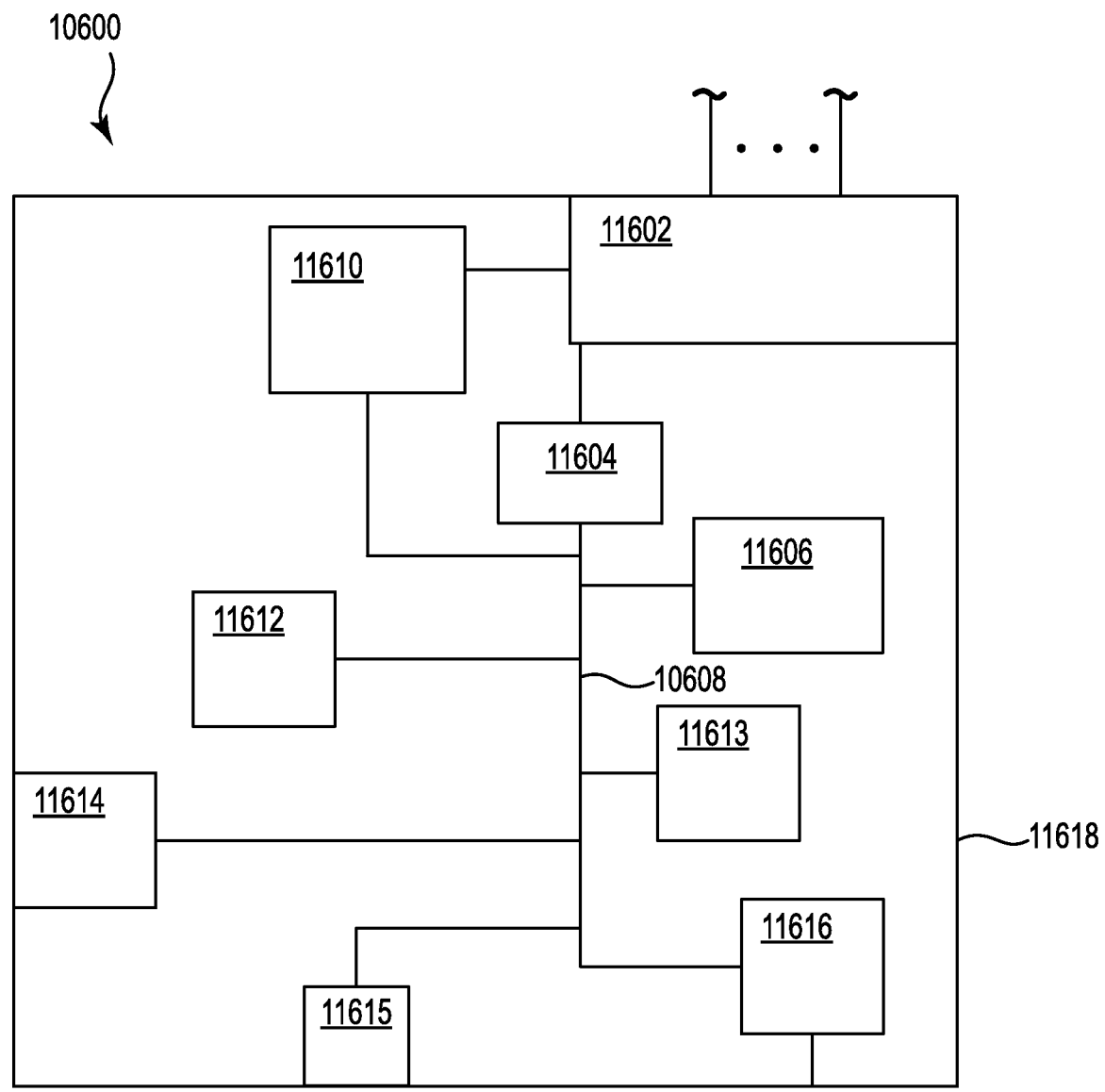
FIG. 11 provides an illustration of a stimulation system for use with the catheter or catheter system of the present system.

Referring now to FIG. 11, there is shown an embodiment of the stimulation system 11600. The stimulation system 11600 includes an input/output connector 11602 that releasably joins the conductive elements of the catheter or catheter system of the present disclosure. It is also possible that the conductive elements 120 are permanently coupled to the stimulation system (e.g., not releasably coupled). An input from the sensor can also be releasably coupled to the input/output connector 11602 so as to receive the sensor signal(s) discussed herein.

The input/output connector 11602 is connected to an analog to digital converter 11604. The output of the analog to digital converter 11604 is connected to a microprocessor 11606 through a peripheral bus 11608 including address, data and control lines. Microprocessor 11606 can process the sensor data, when present, in different ways depending on the type of sensor in use. The microprocessor 11606 can also control, as discussed herein, the pulse control output generator 11610 that delivers the stimulation electrical energy to the one or more electrodes via the input/output connector 11602.

The parameters of the stimulation electrical energy can be controlled and adjusted, as needed, by instructions programmed in a memory 11612 and executed by a programmable pulse generator 11613. The instructions in memory 11612 for the programmable pulse generator 11613 can be set and/or modified based on input from the closed-looped system, via the microprocessor 11606. The instructions in memory 11612 for the programmable pulse generator 11613 can also be set and/or modified through inputs from a professional via an input 11614 connected through the peripheral bus 11608. Examples of such an input include a keyboard with a display screen or through a touch screen (not shown), as are known. The stimulation system 11600 can also include a communications port 11615 that connects to the peripheral bus 11608, where data and/or programming instructions can be received by the microprocessor 11606 and/or the memory 11612.

Input from either a professional via the input 11614, the communications port 11615 or from the closed-looped system via the microprocessor 11606 can be used to change (e.g., adjust) the parameters of the stimulation electrical energy. The stimulation system 11600 can also include a power source 11616. The power source 11616 can be a battery or a power source supplied from an external power supply (e.g., an AC/DC power converter coupled to an AC source). The programmable pulse generator 11612 can also include a housing 11618.

The microprocessor 11606 can execute one or more algorithms in order to provide stimulation with closed loop feedback control. The microprocessor 11606 can also be controlled by a professional via the input 11614 to initiate, terminate and/or change (e.g., adjust) the parameters of the stimulation electrical energy. The closed loop feedback control can be used to help maintain one or more of a patient's cardiac parameters at or within a threshold value or range programmed into memory 11612. For example, under closed loop feedback control measured cardiac parameter value(s) can be compared and then it can be determine whether or not the measured value(s) lies outside a threshold value or a pre-determined range of values. If the measured cardiac parameter value(s) do not fall outside of the threshold value or the pre-determined range of values, the closed loop feedback control continues to monitor the cardiac parameter value(s) and repeats the comparison on a regular interval. If, however, the cardiac parameter value(s) from a sensor indicate that one or more cardiac parameters are outside of the threshold value or the pre-determined range of values one or more of the parameters of the stimulation electrical energy will be adjusted by the microprocessor 11606. The adjustments can be made using process control logic (e.g., fuzzy logic, negative feedback, etc.) so as to maintain control of the pulse control output generator 11610.

Although preferred illustrative variations of the present disclosure are described above, it will be apparent to those skilled in the art that various changes and modifications may be made thereto without departing from the embodiments of the present disclosure. It is intended in the appended claims to cover all such changes and modifications that fall within the true spirit and scope of the disclosure.

What is claimed is:

1. A catheter for treating acute heart failure by applying electrical neuromodulation, the catheter comprising:
    an elongate body having a first end, a second end, and a longitudinal axis, a first plane including the longitudinal axis;
    at least two elongate stimulation members configured to extend from the elongate body, each of the at least two elongate stimulation members comprising an electrode, each of the at least two elongate stimulation members configured to curve into a first volume on a first side of the first plane to form an electrode array in the first volume, at least one of the at least two elongate stimulation members including:
        a stimulation member elongate body; and
        a first portion of a wire extending longitudinally through the stimulation member elongate body, the first portion of the wire distal to a second portion of the wire extending longitudinally through the elongate body,
        wherein application of pressure by the wire against the stimulation member elongate body at or near a distal end of the stimulation member elongate body causes the wire to deflect to impart the curve to the at least one elongate stimulation member;
    conductive elements extending through each of the at least two elongate stimulation members, the conductive elements configured to conduct electrical current to combinations of two or more of the electrodes in the electrode array;
    an anchor member configured to extend from the elongate body into a second volume on a second side of the first plane, the second side opposite the first side, wherein the anchor member does not include an electrode;
    a sensor comprising at least one of a blood oxygen sensor, a pressure sensor, and an integrated circuit;
    a sensor conductive element extending through the elongate body, the sensor conductive element configured to conduct electrical signals from the sensor;
    a structure extending between at least two of the least two elongate stimulation members, the structure comprising a mesh structure comprising insulated flexible strands connected to form a pattern of openings between the elongate stimulation members; and
    an additional electrode positioned on the structure at an intersection of the flexible strands.

2. The catheter of claim 1, wherein the at least two elongate stimulation members curve only in the first volume, and wherein the second volume contains no electrodes, wherein a second plane including the longitudinal axis perpendicularly intersects the first plane to divide the first volume into a first quadrant volume and a second quadrant volume, and wherein the at least two elongate stimulation members include a first elongate stimulation member and a second elongate stimulation member, the first elongate stimulation member configured to curve into the first quadrant volume and the second elongate stimulation member configured to curve into the second quadrant volume.

3. A catheter system comprising:
    a catheter of claim 1; and
    a pulmonary artery catheter having a lumen, wherein the catheter extends through the lumen of the pulmonary artery catheter, the pulmonary artery catheter including:
        an elongate pulmonary catheter body comprising:
            a first end,
            a second end,
            a peripheral surface, and
            an interior surface at least partially defining the lumen of the pulmonary artery catheter;
        an inflatable balloon on the peripheral surface; and
        an inflation lumen extending through the elongate pulmonary catheter body, the inflation lumen having an opening configured to allow fluid to inflate and deflate the inflatable balloon.

4. A catheter for treating acute heart failure by applying electrical neuromodulation, the catheter comprising:
    an elongate body having a first end, a second end, and a longitudinal axis, a first plane including the longitudinal axis;
    at least two elongate stimulation members configured to extend from the elongate body, each of the at least two elongate stimulation members comprising a proximal end, a distal end, and an electrode, each of the at least two elongate stimulation members configured to curve into a first volume on a first side of the first plane to form an electrode array in the first volume, at least one of the at least two elongate stimulation members including:
        a stimulation member elongate body; and
        a first portion of a wire extending longitudinally through the stimulation member elongate body, the first portion of the wire distal to a second portion of the wire extending longitudinally through the elongate body,
        wherein application of pressure by the wire against the stimulation member elongate body at or near a distal end of the stimulation member elongate body causes the wire to deflect to impart the curve to the at least one elongate stimulation member;
    conductive elements extending through each of the at least two elongate stimulation members, the conductive elements configured to conduct electrical current to combinations of two or more of the electrodes in the electrode array;
    an anchor member configured to extend from the elongate body into a second volume on a second side of the first plane, the second side opposite the first side, wherein the anchor member does not include an electrode;
    a mesh structure extending across and between the proximal and distal ends of at least two of the at least two elongate stimulation members; and
    an additional electrode positioned on the structure.

5. The catheter of claim 4, wherein the at least two elongate stimulation members curve only in the first volume, and wherein the second volume contains no electrodes.

6. The catheter of claim 4, wherein a second plane including the longitudinal axis perpendicularly intersects the first plane to divide the first volume into a first quadrant volume and a second quadrant volume, and wherein the at least two elongate stimulation members include a first elongate stimulation member and a second elongate stimulation member, the first elongate stimulation member configured to curve into the first quadrant volume and the second elongate stimulation member configured to curve into the second quadrant volume.

7. The catheter of claim 4, further comprising:
a sensor; and
a sensor conductive element extending through the elongate body, wherein the sensor conductive element is configured to conduct electrical signals from the sensor.

8. The catheter of claim 7, wherein the sensor comprises at least one of a blood oxygen sensor, a pressure sensor, and an integrated circuit.

9. A catheter system comprising:
a catheter of claim 4; and
a pulmonary artery catheter having a lumen, wherein the catheter extends through the lumen of the pulmonary artery catheter, the pulmonary artery catheter including:
an elongate pulmonary catheter body comprising:
a first end,
a second end,
a peripheral surface, and
an interior surface at least partially defining the lumen of the pulmonary artery catheter;
an inflatable balloon on the peripheral surface; and
an inflation lumen extending through the elongate pulmonary catheter body, the inflation lumen having an opening configured to allow fluid to inflate and deflate the inflatable balloon.

10. The catheter system of claim 4, wherein the structure is expandable from a delivery state to an expanded state.

11. A catheter for treating acute heart failure by applying electrical neuromodulation, the catheter comprising:
an elongate body having a first end, a second end, and a longitudinal axis, a first plane including the longitudinal axis;
at least two elongate stimulation members configured to extend from the elongate body, each of the at least two elongate stimulation members comprising a plurality of electrodes, each of the at least two elongate stimulation members configured to be in a first volume on a first side of the first plane to form an electrode array in the first volume;
conductive elements extending through each of the at least two elongate stimulation members, the conductive elements configured to conduct electrical current to combinations of two or more of the electrodes in the electrode array;
an anchor member configured to extend from the elongate body into a second volume on a second side of the first plane, the second side opposite the first side, wherein the anchor member does not include an electrode; and
a mesh structure extending across at least two of the at least two elongate stimulation members, the structure comprising a low-profile delivery state and a deployed state, the deployed state including a pre-defined shape configured to locate and position the at least two of the at least two elongate stimulation members.

12. The catheter of claim 11, wherein the at least two elongate stimulation members curve only in the first volume, and wherein the second volume contains no electrodes.

13. The catheter of claim 11, wherein a second plane including the longitudinal axis perpendicularly intersects the first plane to divide the first volume into a first quadrant volume and a second quadrant volume, and wherein the at least two elongate stimulation members include a first elongate stimulation member and a second elongate stimulation member, the first elongate stimulation member configured to curve into the first quadrant volume and the second elongate stimulation member configured to curve into the second quadrant volume.

14. The catheter of claim 11, further comprising:
a sensor; and
a sensor conductive element extending through the elongate body, wherein the sensor conductive element is configured to conduct electrical signals from the sensor.

15. The catheter of claim 14, wherein the sensor comprises at least one of a blood oxygen sensor, a pressure sensor, and an integrated circuit.

16. The catheter of claim 11, further comprising:
wherein at least one of the at least two elongate stimulation members includes:
a stimulation member elongate body; and
a wire extending longitudinally through the stimulation member elongate body,
wherein application of pressure by the wire against the stimulation member elongate body causes the wire to deflect to impart the curve to the at least one elongate stimulation member.

17. A catheter system comprising:
a catheter of claim 11; and
a pulmonary artery catheter having a lumen, wherein the catheter extends through the lumen of the pulmonary artery catheter.

18. The catheter system of claim 17, wherein the pulmonary artery catheter includes:
an elongate pulmonary catheter body comprising:
a first end,
a second end,
a peripheral surface, and
an interior surface at least partially defining the lumen of the pulmonary artery catheter;
an inflatable balloon on the peripheral surface; and
an inflation lumen extending through the elongate pulmonary catheter body, the inflation lumen having an opening configured to allow fluid to inflate and deflate the inflatable balloon.

19. The catheter system of claim 11, further comprising a pressure sensor.

20. The catheter system of claim 11, wherein each of the at least two elongate stimulation members comprises a proximal end and a distal end, and wherein the mesh structure extends across and between the proximal and distal ends of at least two of the at least two elongate stimulation members.

* * * * *